(12) United States Patent
Chung et al.

(10) Patent No.: US 8,058,413 B2
(45) Date of Patent: Nov. 15, 2011

(54) MOLECULAR TRANSPORTERS BASED ON SUGAR AND ITS ANALOGUES AND PROCESSES FOR THE PREPARATION THEREOF

(75) Inventors: Sung-Kee Chung, Pohang-si (KR); Kaustabh Kumar Maiti, Pohang-si (KR); Woo Sirl Lee, Seoul (KR); Ock-Youm Jeon, Seongnam-si (KR); Seok-Ho Lee, Pohang-si (KR)

(73) Assignees: Postech Foundation, Kyungsangbuk-Do (KR); Postech Academy-Industry Foundation, Kyungsangbuk-Do (KR)

( * ) Notice: Subject to any disclaimer, the term of this patent is extended or adjusted under 35 U.S.C. 154(b) by 0 days.

(21) Appl. No.: 12/860,538

(22) Filed: Aug. 20, 2010

(65) Prior Publication Data
US 2010/0330671 A1 Dec. 30, 2010

Related U.S. Application Data

(62) Division of application No. 11/815,339, filed as application No. PCT/KR2005/002040 on Jun. 29, 2005, now Pat. No. 7,846,975.

(30) Foreign Application Priority Data

Apr. 28, 2005 (KR) .................. 10-2005-0035410

(51) Int. Cl.
*C07H 1/00* (2006.01)
*A01N 43/04* (2006.01)
*A61K 31/70* (2006.01)
*A61B 5/055* (2006.01)

(52) U.S. Cl. .................. 536/1.11; 514/25; 424/9.35

(58) Field of Classification Search .................. 514/25; 424/9.35
See application file for complete search history.

(56) References Cited

U.S. PATENT DOCUMENTS
6,495,663 B1 12/2002 Rothbard et al.
2006/0280796 A1* 12/2006 Chung et al. .................. 424/484

FOREIGN PATENT DOCUMENTS
| JP | 2002-502388 A | 1/2002 |
| JP | 2002-544241 A | 12/2002 |
| WO | 7900515 A1 | 8/1979 |
| WO | 92/13955 A1 | 8/1992 |
| WO | 9404686 A1 | 3/1994 |
| WO | 98/54130 A1 | 12/1998 |
| WO | 00/69470 A1 | 11/2000 |

OTHER PUBLICATIONS

Le, G.T., Abbenante, G., Becker, B., Grathwohl, M., Halliday, J., Tometzki, G., Zuegg, J., Meutermans, W. (2003) Molecular diversity through sugar scaffolds. Drug Discovery Today, vol. 8, No. 15, p. 701-709.*

Fawell, S. et al., "Tat-Mediated Delivery of Heterologous Proteins into Cells," Proc. Natl. Acad. Sci. USA., vol. 91: 664-668 (1994).

Brugidou, J., et al., "The Retro-inverso Form of a Homeobox-Derived Short Peptide is Rapidly Internalized by Cultured Neurons: A New Basis for an Efficient Intracellular Delivery System," Biochem. Biophys. Res. Comm., vol. 214: 685-693 (1995).

Wender, P.A., Mitchell, D.J., Pattabiraman, K., Pekley, E.T., Steinman, L., Rothbard, J.B. (2000) The design, synthesis, and evaluation of molecules that enable or enhance cellular uptake: Peptoid molecular transporters. Proceedings of the National Academy of Sciences, vol. 97, No. 24, p. 13003-13008.

* cited by examiner

*Primary Examiner* — Shaojia Anna Jiang
*Assistant Examiner* — Scarlett Goon
(74) *Attorney, Agent, or Firm* — Sughrue Mion, PLLC

(57) ABSTRACT

The inventive molecular transporter compound shows significantly high permeability through a biological membrane such as a plasma membrane, nuclear membrane and blood-brain barrier, and accordingly, can be effectively used in delivering various biologically active molecules.

9 Claims, 2 Drawing Sheets

MOLECULAR TRANSPORTERS BASED ON SUGAR AND ITS ANALOGUES AND PROCESSES FOR THE PREPARATION THEREOF

This is a divisional of U.S. application Ser. No. 11/815,339 filed Aug. 2, 2007 now U.S. Pat. No. 7,846,975 which claims priority from PCT/KR2005/00240, filed Jun. 29, 2005, which claims priority from Korean Application No. 10-2005-0035410 filed Apr. 28, 2005. The entire disclosures of the prior applications are hereby incorporated by reference.

FIELD OF THE INVENTION

The present invention relates to molecular transporters having improved membrane permeability, which are consisted of multiple residues of guanidine groups and a sugar skeleton or its analogue, and processes for the preparation thereof.

BACKGROUND OF THE INVENTION

The plasma membrane of a cell separates the cytoplasm of the cell from the environment, and it is primarily composed of a phospholipid bilayer and proteins embedded within the bilayer or attached to the surface thereof. Normally the plasma membrane functions as a gatekeeper, which controls trafficking of essential substances into and out of the cell. However, the cell plasma membrane also functions as permeability barrier and blocks the passage of many useful therapeutic agents. Generally, hydrophilic molecules, highly charged molecules and macromolecules such as nucleic acid or gene cannot readily cross the cell membranes. Therefore, there is a need for a reliable means of transporting drugs and macromolecules into the cell.

Heretofore, a number of transporter molecules such as lipids, polymers and dendrimers have been proposed to escort molecules across biological membranes, but often they are not easily water soluble or biodegradable, and hence, precipitate in a cell to illicit toxicity.

Proteins having a PTD (protein transduction domain) that allows the protein permeation through the plasma membrane include the HIV-1 Tat peptide, Antennapedia (Antp) homeodomain protein, Herpes virus protein VP22, Nuclear localization signal (NLS) sequence, and the like, as shown in Table 1.

TABLE 1

| Protein having PTD | Amino acid sequence | SEQ ID NO: |
|---|---|---|
| HIV-1 Tat (48-60 a.a.) | GRKKRRQRRRPPQ | 1 |
| Antp (43-58 a.a.) | RQIKIWFQNRRMKWKK | 2 |
| VP22 (267-300 a.a.) | DAATATRGRSAASRPTERDRAPARS ASRPRRPVE | 3 |
| SV40-NLS | PKKKRKVC | 4 |
| Nucleoplasmin | KRPAAIKKAGQAKKKKC | 5 |
| NF-κB | PMLKQRKRQA | 6 |
| HIV-1 Rev (34-50 a.a.) | RQARRNRRRRWRERQRG | 7 |
| FHV Coat (35-49 a.a.) | RRRNRTRRNRRRVRRGC | 8 |

TABLE 1-continued

The above protein domains seem to facilitate the permeation across biological membranes without the help of any specific transporter or receptor associated with the cell. Further, they contain a high percentage of basic amino acids such as arginine and lysine. The basic region (i.e., 49-57 a.a.) of the Tat protein, which is a necessary transacting transcriptional activator of HIV virus reproduction, has been reported to play a critical role in the process of the protein permeation through the plasma membrane. A number of studies have reported syntheses of various oligopeptides having a multiple units of arginine and used them as molecular transporters.

From these studies, it has been found that oligomers having eight to nine arginine residues show the highest permeability, and are most effective in enhancing the transportation of molecules attached thereto across a biological membrane, which suggests that the guanidine group of arginine plays an essential role in the transportation of molecules attached thereto across a biological membrane.

Wender et al. designed peptoid molecular transporters based on the fact that the biological membrane permeability of a peptide largely depends on the number of the guanidine group in the peptide, the length of the linker chain, and chirality, etc. It was found that an L-arginine nonamer is 20-times more effective in the transportation across a biological membrane than Tat protein (49-57 a.a.), and D-arginine nonamer was also significantly more effective in the uptake by Jurkat cells, as was determined using FACS (P. A. Wender, et al., Proc. Natl. Acad. Sci. U.S.A. 97: 13003, 2000). These results suggest that the permeability of peptides having a certain number of guanidine groups is not significantly affected by the chirality of the amino acid (U.S. Pat. No. 6,495,663; Korean Patent Laid-Open Publication No. 2001-12809).

However, such polyarginine peptide or related peptoid molecules have problems of rapid metabolism to be eliminated through the liver and kidney as well as their in vivo toxicity liability. Further, the fact that a peptide or peptoid having a number of guanidine groups can maintain its helical structure only in a basic environment suggests that its membrane permeability depends largely on the positively charged guanidinium groups rather then the secondary or tertiary structure thereof.

The present inventors have therefore endeavored to develop molecular transporters prepared by introducing positively charged guanidinium groups to sugar or its analogue structure in a linear or branched form with a high density of functionality and found that such molecular transporters significantly enhance the transport of various physiologically active molecules attached thereto either covalently or ionically, across a biological membrane.

SUMMARY OF THE INVENTION

Accordingly, it is an object of the present invention to provide sugar or its analogue-based molecular transporters having improved permeability, which are effective in the transportation of a physiologically active molecule across a biological membrane and processes for the preparation thereof.

It is another object of the present invention to provide a composition for delivering a physiologically active molecule into a cell, comprising the sugar or its analogue-based molecular transporter.

It is a further object of the present invention to provide a method for delivering a physiologically active molecule into a cell, employing the sugar or its analogue-based molecular transporter.

BRIEF DESCRIPTION OF THE DRAWINGS

The above and other objects and features of the present invention will become apparent from the following description of the invention, when taken in conjunction with the accompanying drawings, which respectively show.

DETAILED DESCRIPTION OF THE INVENTION

Figure 1:
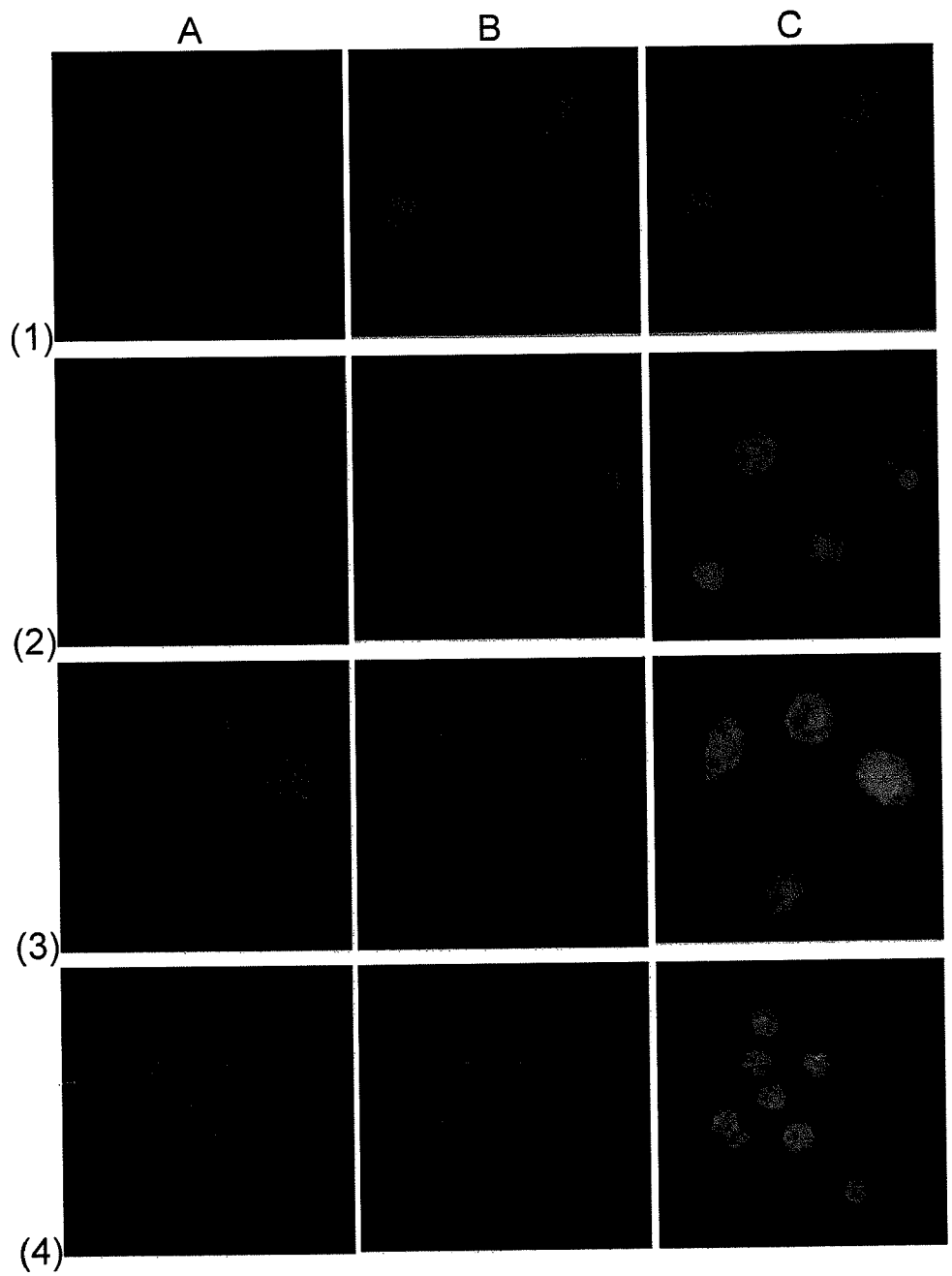
FIG. 1: comparative degrees of cellular and nuclear membrane transmission of various compounds; dansyl-$Arg_9$ (1); the intermediate prepared in Preparation Example 1 having no guanidine group (2), and the transporter compounds obtained in Examples 1 and 6 having 8 and 7 guanidine residues, respectively in accordance with the present invention (3 and 4)

In accordance with one aspect of the present invention, there is provided sugar or sugar analogue-based molecular transporter compounds of formulae 1 to 5, each of which has a linear or branched form of guanidine groups:

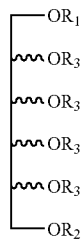

<Formula 1> wherein, $R_1$ and $R_2$ are each independently H, alkyl, arylalkyl, cycloalkyl, heteroalkyl, —$(CH_2)_m NHR'$, —$(CH_2)_l CO_2 R''$, —$COR'''$, —$SO_2 R''''$ or a physiologically active molecule; R', R'', R''' and R'''' being each independently H, alkyl, arylalkyl, cycloalkyl, heteroalkyl or a physiologically active molecule; m, an integer in the range of 2 to 5; and l, an integer in the range of 1 to 5;

$R_3$ is

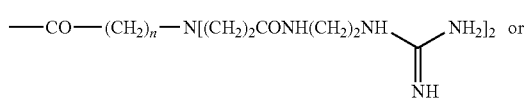

-continued

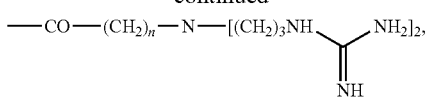

n being an integer in the range of 1 to 12.

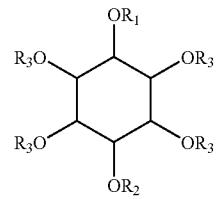

<Formula 2> wherein, $R_1$ and $R_2$ are each independently H, alkyl, arylalkyl, cycloalkyl, heteroalkyl, —$(CH_2)_m NHR'$, —$(CH_2)_l CO_2 R''$, —$COR'''$, —$SO_2 R''''$ or a physiologically active molecule; R', R'', R''' and R'''' being each independently H, alkyl, arylalkyl, cycloalkyl, heteroalkyl or a physiologically active molecule; m, an integer in the range of 2 to 5; and l, an integer in the range of 1 to 5;

$R_3$ is

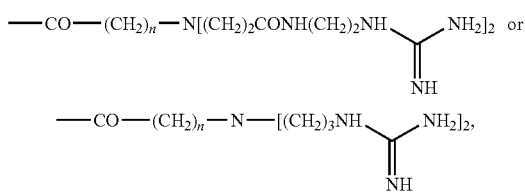

n being an integer in the range of 1 to 12.

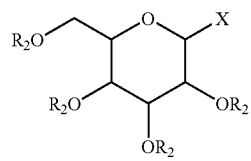

<Formula 3> wherein,

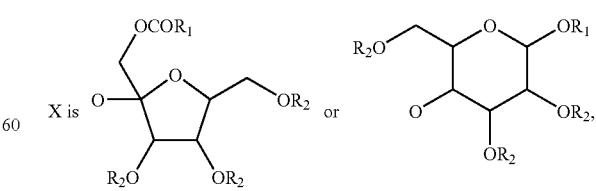

$R_1$ being —$(CH_2)_m NHR'$, in which m is an integer in the range of 2 to 9, and R' is H, alkyl, arylalkyl, cycloalkyl, heteroalkyl or a physiologically active molecule;

$R_2$ is

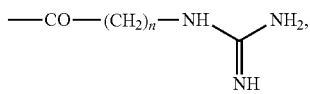

n being an integer in the range of 1 to 12.

<Formula 4>

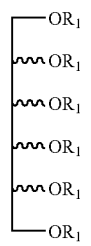

wherein,
$R_1$ is

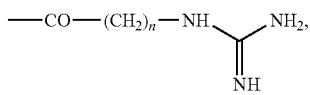

n being an integer in the range of 1 to 12.

<Formula 5>

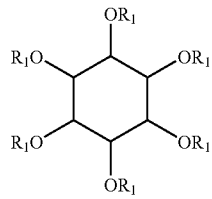

wherein,
$R_1$ is

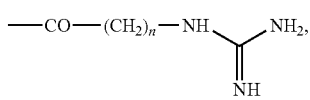

n being an integer in the range of 1 to 12.

The compounds of formulae 1 and 2 according to the present invention are molecular transporters having eight guanidine groups introduced at the hydroxy terminals of a sugar derivative, which is capable of holding the target functional group in its skeleton at a high density when branched chains are introduced therein. The compound of formula 1 includes an alditol derivative and its salt having a skeleton of sorbitol, mannitol or galactitol, which is exemplified by a sorbitol derivative of formula 6. Further, the compound of formula 2 includes an inositol derivative and its salt having a skeleton of myo-inositol or scyllo-inositol, which is exemplified by compounds of formulae 7 to 9.

<Formula 6>

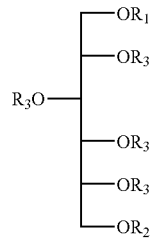

<Formula 7>

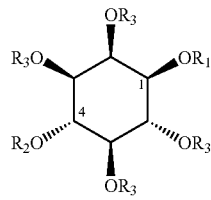

<Formula 8>

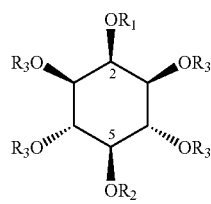

<Formula 9>

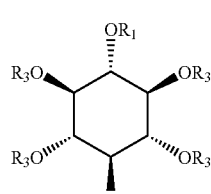

wherein,
$R_1$, $R_2$ and $R_3$ are the same as defined in formulae 1 and 2.

Further, the molecular transporter compound of formula 3 has a disaccharide skeleton having seven guanidine groups in the side chains, and preferred examples thereof are represented by compounds of formulae 10 and 11 and their salts.

<Formula 10>

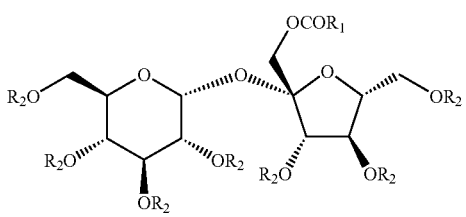

<Formula 11>

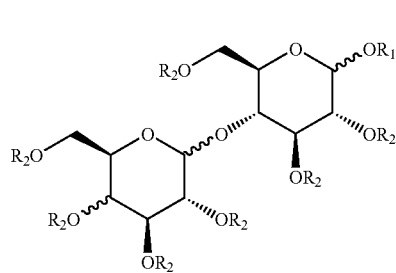

wherein,

R$_1$ and R$_2$ are the same as defined in formula 3.

The compounds of formulae of 10 and 11 are disaccharide derivatives, wherein the compound of formula 10 has a skeleton of sucrose and that of formula 11, α-lactose, β-lactose or maltose.

The compounds of formulae 4 and 5 are the molecular transporters having six guanidine groups attached to sugar derivatives. The compounds of formula 4 include an alditol derivative and its salt having a skeleton of sorbitol, mannitol or galactitol, and are exemplified by a sorbitol derivative of formula 12 and its salt. Further, the compounds of formula 5 include an inositol derivative and its salt having a skeleton of myo-inositol or scyllo-inositol, and are exemplified by compounds of formulae 13 to 14 and their salts.

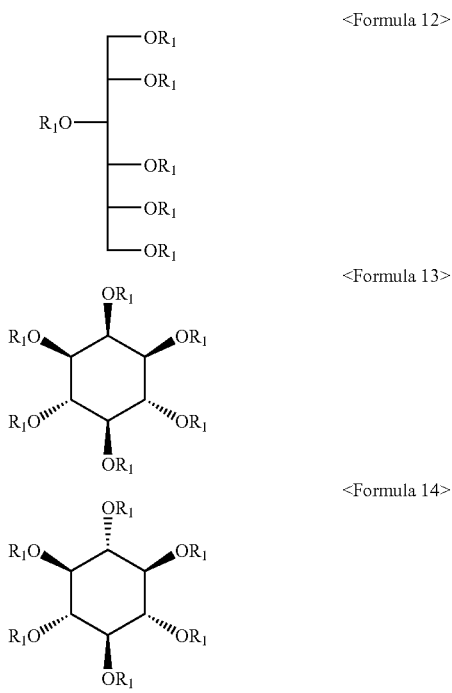

<Formula 12>

<Formula 13>

<Formula 14> wherein,

R$_1$ is the same as defined in formulae 4 and 5.

The molecular transporter compounds of formula 1 to 5, more specifically compounds of formulae 6 to 14, have functional groups capable of coupling to a physiologically active molecule, and therefore, can easily transport the target molecule attached thereto across a biological membrane. Here, the physiologically active molecule means a natural, synthetic or genetically engineered chemical or biological compound that is known in the art as having utility for modulating physiological processes in order to afford diagnosis of, prophylaxis against, or treatment of, an undesired existing condition in a living being. Preferably, the physiologically active molecule being delivered into a cell by coupling to the molecular transporter compounds of the present invention includes organic compounds having a molecular weight ranging from 100 to 1,500 g/mol, a polymer such as a peptide and nucleic acid, and a diagnostic reagent. As shown in formulae 6 to 14, the molecular transporter compounds of the present invention have a sugar or sugar analogue skeleton carrying guanidine groups through a linear or branched chain of variable chain lengths, and therefore, each of them shows a good water-solubility and membrane permeability. Accordingly, the molecular transporter compounds in accordance with the present invention can be attached to a physiologically active molecule such as a drug, diagnostic reagent or fluorescent tag through either a covalent bond or an ionic bond so that it can be easily transported across a biological membrane, e.g., plasma membrane, nuclear membrane or blood-brain barrier.

Further, the present invention provides a method for preparing the molecular transporter compounds in accordance with the present invention, comprising the following steps of:

1) introducing amino acid side chains via acylation of the hydroxyl groups to obtain an intermediate compound;

2) introducing protected guanidine groups to the terminal amino groups of the amino acid side chains of the compound obtained in step 1); and 3) removing the protecting groups from the compound obtained in step 2) to provide the molecular transporter compounds.

Here, instead of steps 1) and 2) in the above method, it is also possible to prepare first the terminal amino acid side chains with the protected guanidine groups, and then to introduce the pre-prepared side chains to the hydroxyl groups of the protected skeletal intermediate by acylation.

More specifically, the method for the preparation of the molecular transporters in accordance with the present invention can be explained depending on the kind of sugar or its analogue skeleton, as follows.

The molecular transporter compounds of formulae 1 and 2, preferably formulae 6 to 9, are prepared by the following steps employing the intermediates of formulae 15 to 18 as starting materials, respectively;

1) introducing the amino acid side chains to the hydroxyl groups of the protected intermediate by acylation;

2) removing the protecting groups from the terminal amino acid side chains;

3) introducing the guanidine groups to the terminal amino groups of the amino acid side chains;

4) removing the protecting groups from the hydroxyl groups of the compound obtained in step 3) and coupling it to a physiologically active molecule; and 5) removing the amino protecting groups from the guanidine groups of the compound obtained in step 4).

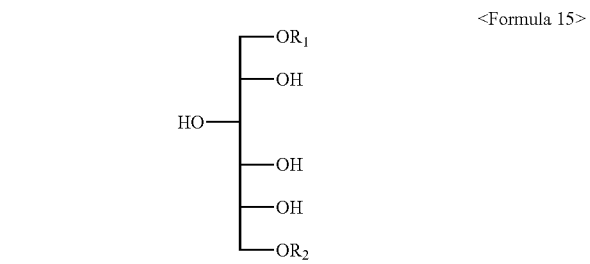

<Formula 15>

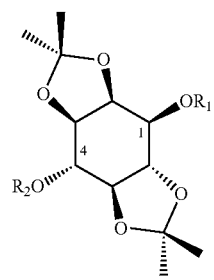

<Formula 16>

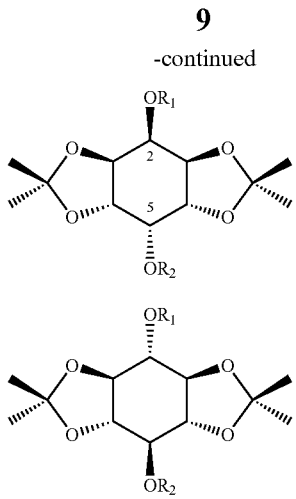

<Formula 17>

<Formula 18> wherein, $R_1$ and $R_2$ are the same as defined in formulae 1 and 2.

The compound of formula 15, a key intermediate for preparing the compound of formula 6, is an alditol derivative having introduced protecting groups at 1,6-OH positions of D-aldohexose such as D-glucose regioselectively, and can be prepared according to the procedure of Scheme 1:

<Scheme 1>

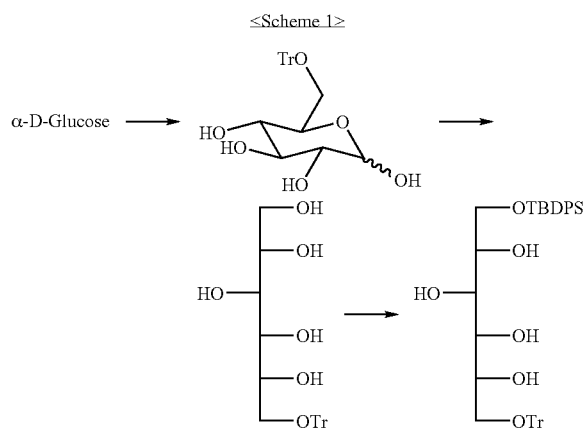

According to Scheme 1 exemplified with D-glucose as a starting material, the intermediate of formula 15 ($R_1$=TBDPS, $R_2$=Tr) can be prepared by selectively introducing a trityl (Tr) protecting group to 6-OH of D-glucose; performing a reduction reaction by using a reducing agent such as sodium borohydride ($NaBH_4$), to obtain D-sorbitol in a linear form; and selectively introducing t-butyldiphenylsilyl (TBDPS) group to 1-OH thereof.

Further, the intermediate of formula 16 for preparing the compound of formula 7 can be prepared by synthesizing 2,3:5,6-di-O-isopropylidene-myo-inositol from myo-inositol; and introducing different protecting groups, e.g., tert-butyldimethylsilyl (TBDMS) or benzyl (Bn) protecting group, to 1-OH or 4-OH thereof regioselectively.

The intermediate of formula 17 for preparing the compound of formula 8 can be prepared by synthesizing 1,6:3,4-di-O-isopropylidene-myo-inositol from myo-inositol; and introducing different protecting groups, e.g., p-methoxybenzyl (PMB) or benzyl (Bn) protecting group, to 2-OH or 5-OH thereof regioselectively.

Further, the intermediate of formula 18 for preparing the compound of formula 9 can be prepared by inverting the stereochemistry of 2-OH of myo-inositol through Mitsunobu reaction; synthesizing 1,6:2,4-di-O-isopropylene-scyllo-inositol therefrom; and introducing different protecting groups, e.g., PMB, benzoyl (Bz) or Bn protecting group, to 2-OH or 5-OH thereof regioselectively.

In step 1), the amino acid side chains of various lengths are introduced to the protected intermediate by acylation as described above. The intermediates of formulae 16 to 18 except the intermediate of formula 15 are subjected to deprotection of the acetonide protecting groups before the acylation reaction. The acylation reaction is carried out by reacting each intermediate with the amino acid having variable chain lengths with the protected amino groups as carbobenzyloxy (Cbz) groups, in the presence of a condensing agent such as dicyclohexylcarbodiimide and 1-[3-(dimethylamino)propyl]-ethylcarbodiimide hydrochloride. The amino acid having variable chain lengths employed in the present invention can be obtained from commercially available ω (omega)-amino acid, and N,N-di-aminopropyl aminocaproic acid derivatives having the protected terminal amino groups with appropriate protecting groups is preferable.

The above acylation reaction may be conducted using the amino acid having variable chain lengths in an amount ranging from 1.5 to 2.5 equivalents based on 1 equivalent of functionality of each intermediate at a temperature ranging from 25 to 40° C. for 16 to 72 hrs.

In step 2), the amino protecting groups are removed from the terminal amino groups of the side chains. The deprotection may be performed by adding a catalyst such as palladium (Pd), nickel and platinum to the compound obtained in step 1), stirring the mixture under a hydrogen atmosphere and filtering.

In step 3), the deprotected amino groups of the compound obtained in step 2) are converted into guanidine groups by reacting the compound with N,N'-di-Boc-N"-triflylguanidine or N,N'-di-Boc-S-methylisothiourea in the presence of a base in an organic solvent (T. T. Baker, et al., *J. Org. Chem.* 65: 9054, 2000; A. E. Miller and J. J. Bischoff, *Synthesis* 777, 1986). Instead, it is possible that the guanidine groups are introduced to the terminal amine resides of the side chains in advance, and then, the pre-prepared side chains having the guanidine groups are directly introduced to the intermediate skeleton by acylation. Exemplary organic solvents that may be used in the above step are dichloromethane, N,N-dimethylformamide, chloroform, ethyl acetate, 1,4-dioxane, and the like, and the base may be triethylamine. The above reaction may be carried out at a temperature ranging from 25 to 40° C. for 16 to 72 hrs.

In step 4), the protecting groups are removed from the compound obtained in step 3), and the exposed hydroxyl groups may be used in coupling to a physiologically active molecule or its derivative. It is also possible to introduce a fluorescent tag such as dansyl (5-dimethylamino-1-naphthalene sulfonyl), FITC (Fluorescein) and Rhodamine to the compound by eliminating one of the protecting groups selectively from the compound having the guanidine groups, and then attaching the fluorescent marker.

Finally, the protecting groups are eliminated from the guanidine groups of the compound obtained in step 4), to obtain the molecular transporter compounds of formulae 6 to 9 in accordance with the present invention.

Scheme 2 illustrates the procedure for preparing the molecular transporter of formula 6 from the intermediate of formula 15.

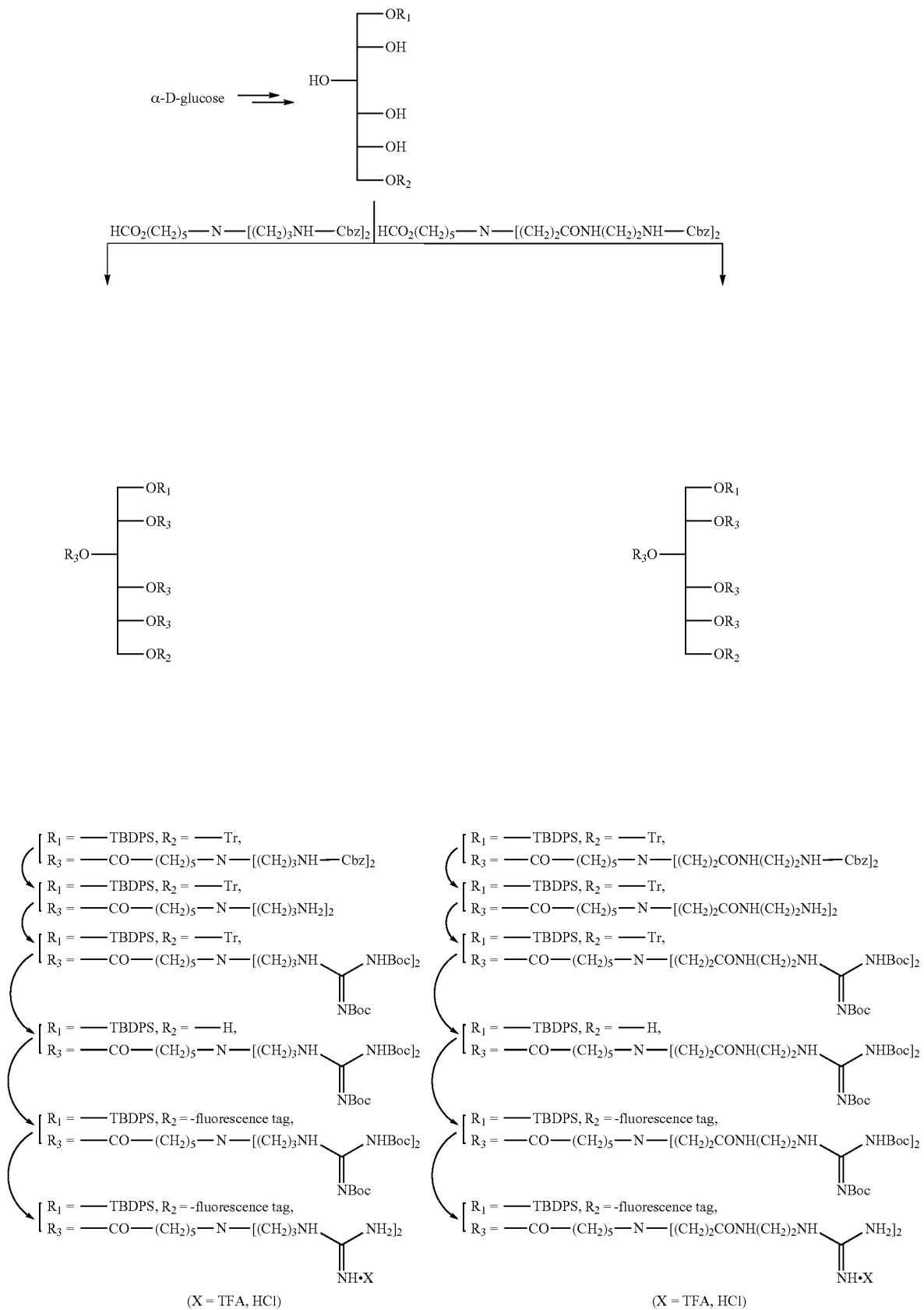

Further, the compounds of formulae 10 and 11 used as representative examples of the molecular transporters having a disaccharide skeleton may each be prepared from the intermediates of formulae 19 and 20 according to the same procedure as shown in Scheme 2.

<Formula 19>

<Formula 20>

The intermediates of formulae 19 and 20 may be used for preparing the compounds of formulae 10 and 11 by introducing the side chains to 1'-OH or 1-OH of sucrose and lactose, regioselectively. More specifically, the intermediate of formula 19 is prepared by selectively introducing the preformed side chains to 1'-OH of sucrose by using enzymes such as proteinase N; and the intermediate of formula 20 is prepared by carrying out benzoylation of lactose, selectively removing the benzoate protecting group from the 1-OH position thereof, and then performing a glycosylation of the sugar derivative with the side chain alcohol.

The compound of formula 10 may be prepared by performing acylation of the intermediate of formula 19 with ω-amino acids having variable chain lengths protected with N-Boc (N-tert-butyloxycarbonyl) such as 4-aminobutanic acid, 6-aminocaproic acid and 8-aminocaprilic acid; removing the protecting groups from the terminal amine residues thereof; and introducing guanidine groups thereto. After the azido functional group of the compound of formula 10 thus prepared is converted by reduction into an amino group in the presence of palladium catalyst and hydrogen atmosphere, it is possible to couple a biologically active molecule such as a drug, a fluorescent tag and a diagnostic reagent to the amino group.

The compound of formula 11 may be prepared by removing benzoate protecting groups from the intermediate of formula 20; introducing ω-amino acids having variable chain lengths thereto by acylation; removing the protecting groups from the terminal amino residues thereof; and introducing the guanidine groups thereto, according to the same method as described above in the preparation of the compound of formula 10.

Scheme 3 illustrates the procedure of preparing the compound of formula 10 from the intermediate of formula 19.

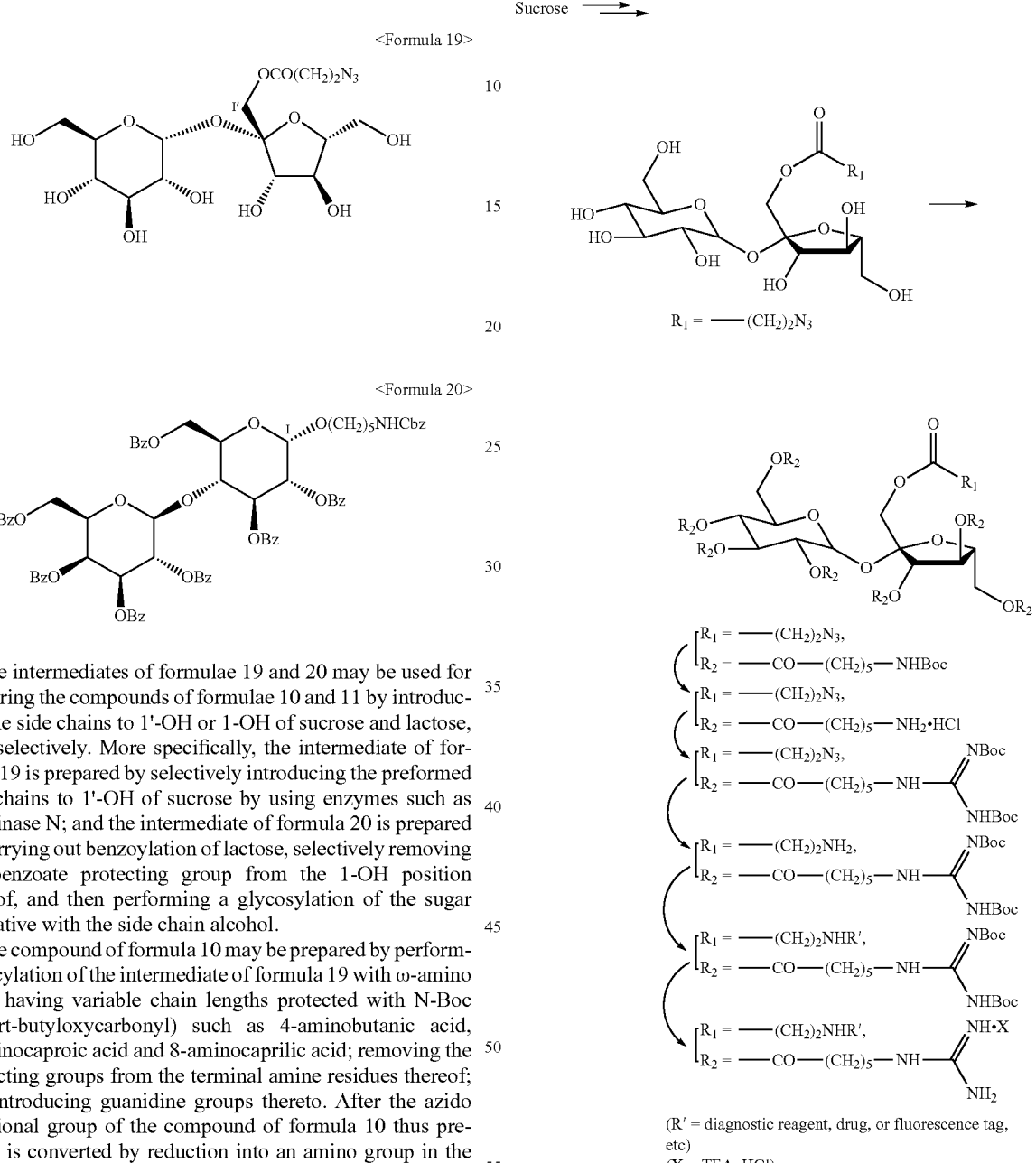

Furthermore, the compounds of formulae 4 and 5 having 6 guanidine groups, more specifically the compounds of formulae 12 to 14, may be prepared by using alditols including D-sorbitol of formula 21 (J. S Brimacombe and J. M. Webber in "The Carbohydrate: Chemistry and Biochemistry", Ed. W. Pigman, D. Horton, 2nd Ed. 1A, Academic Press, 1972) or any of the stereoisomers of inositol including myo- and scyllo-inositol of formulae 22 and 23 (Y. U. Kwon, et al., *J. Org. Chem.* 67: 3327, 2002) as an intermediate.

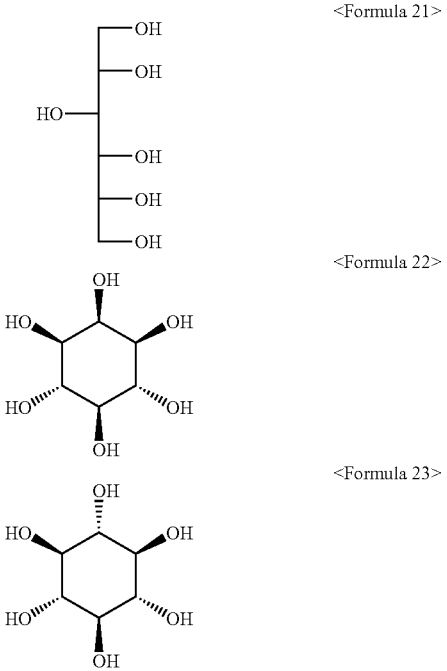

<Formula 21>
<Formula 22>
<Formula 23>

As shown in Scheme 4, the amino acid side chains having variable chain lengths protected with N-Boc are introduced to each of all hydroxyl groups of myo-inositol of formula 22 by acylation. After the N-Boc protecting groups are eliminated and the guanidine groups are introduced thereto, the protecting groups are removed by using TFA (trifluoroacetic acid) or gaseous HCl, to obtain the compound of formula 13. The compounds of formulae 12 and 14 can be prepared from the intermediates of formula 21 and 23, respectively, according to the same method as described above.

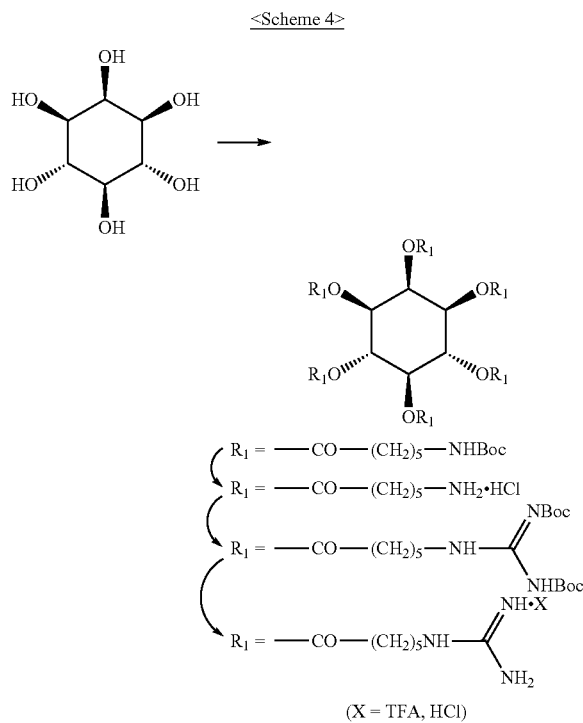

The molecular transporter compounds in accordance with the present invention are sugar or sugar analogue-based derivatives having 6 to 8 guanidine groups, and may be conjugated with biologically active molecules such as a drug, or a diagnostic reagent by way of forming a covalent bond or an ionic bond. The conjugate thus formed shows a significantly enhanced uptake by the cells, indicating that biological barriers such as a plasma membrane, nuclear membrane and blood-brain barrier have been overcome.

Accordingly, the molecular transporter compounds of the present invention may be effectively used in delivering polymers such as peptide and nucleic acids as well as various therapeutic molecules such as drugs and diagnostic reagents into cells.

Therefore, the present invention provides a composition for delivering a physiologically active molecule into cells across the biological membrane, comprising one of the molecular transporter compounds of formula 1 to 5. Further, the present invention provides a method for delivering a physiologically active molecule into a cell across a biological membrane, employing one of the molecular transporter compounds of formula 1 to 5.

The biologically active molecule which can be attached to the molecular transporters of the present invention and delivered into cells includes an organic compound having a molecular weight ranging from 100 to 1500 g/mol and a polymeric compound such as a peptide and a nucleic acid. The molecular transporter compounds of formula 1 to 5 can deliver a biologically active molecule into cells by way of forming an ionic complex through an ionic bond, and the molecular transporter compounds of formula 1 to 3 in particular can each form a conjugate with a biologically active molecule through a covalent bond as well as an ionic bond.

The following Examples are intended to further illustrate the present invention without limiting its scope.

Preparation Example 1

Preparation of Sorbitol Having Protecting Groups

<1-1> Introduction of Trityl Protecting Group to α-D Glucose

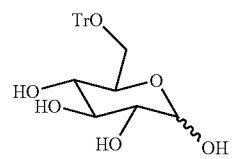

α-D-Glucose (10 g, 55.5 mmol) was dissolved in 120 ml of dry pyridine, and triethylamine (38.7 ml, 277.5 mmol) was added thereto. Tritylchloride (18.3 g, 65.5 mmol) was added dropwise to the mixture, and the mixture was stirred for a day. After the reaction was completed, the reaction mixture was diluted with dichloromethane ($CH_2Cl_2$, 250 ml) and washed with saturated $NaHCO_3$ (300 ml). The organic layer thus obtained was dried over $Na_2SO_4$, concentrated under a reduced pressure, and purified by column chromatography (ethyl acetate:n-hexane=2:3 to 1:1 to 3:2), to obtain the title compound as a light brownish solid (16.87 g).

$^1$H-NMR ($CD_3OD$): δ 3.25-3.38 (m, 4H), 3.59 (t, J=9.2 Hz, 1H), 3.94 (m, 1H), 5.13 (d, J=3.7 Hz, 2H), 7.11-7.30 (m, 9H), 7.42 (d, J=9.4 Hz, 6H)

MS (FAB) m/z 445.22 ($M^+$+Na)

<1-2> Preparation of Sorbitol from the Protected α-D-Glucose

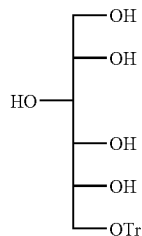

The compound obtained in Preparation Example <1-1> (10 g, 23.66 mmol) was dissolved in methanol (200 ml), sodium borohydride (NaBH$_4$) (2.18 g, 59.18 mmol) was added portionwise thereto, and then, the mixture was stirred at room temperature for 7 hrs. The reaction mixture was concentrated under a reduced pressure, and crystallized from a mixture of water and methanol, to obtain the title compound as a white solid (6.68 g).

$^1$H-NMR (CD$_3$OD): δ 3.25-3.33 (m, 4H), 3.47-3.51 (m, 2H), 3.85-3.87 (m, 2H), 7.14-7.26 (m, 9H), 7.42 (d, J=8.8 Hz, 6H)

MS (FAB) m/z 447.29 (M$^+$+Na)

<1-3> Introduction of t-butyldiphenylsilyl Protecting Group

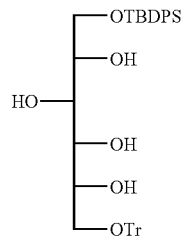

The compound obtained in Preparation Example <1-2> (5 g, 11.77 mmol), triethylamine (4.9 ml, 35.33 mmol) and (4-dimethylamino-pyridine (287.8 mg, 0.235 mmol) were dissolved in N,N-dimethylformamide (50 ml). tert-Butylchlorodiphenylsilane (6.12 ml, 23.55 mmol) was added dropwise to the above mixture over a period of an hour, and the resulting mixture was stirred for a day at room temperature. After the reaction was completed, the reaction solution was diluted with ethyl acetate (200 ml) and washed successively with water (150 ml) and saturated NaCl (25 ml). The aqueous layer thus obtained was re-extracted twice with ethyl acetate (50 ml), and the combined organic layer was dried over Na$_2$SO$_4$, concentrated under a reduced pressure, and subjected to column chromatography (ethyl acetate:n-hexane=1:1 to 3:2), to obtain the title compound as a white foamy solid (5.5 g).

$^1$H-NMR (CDCl$_3$): δ 1.06 (s, 9H), 2.72 (brs, 1H), 3.01 (brs, 1H), 3.21 (brs, 1H), 3.35 (d, J=5.5 Hz, 2H), 3.73-3.83 (m, 6H), 7.22-7.65 (m, 25H)

MS (FAB) m/z 686.24 (M$^+$+Na)

Preparation Example 2

Preparation of Aminocaproic Acid Derivative Having Carbobenzoxy Protecting Groups (I)

<2-1> Preparation of N-di-cyanoethylated 6-aminocaproic Acid

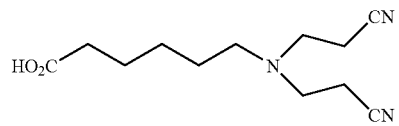

An excess amount of acrylonitrile (94.1 ml, 1.43 mol) and glacial acetic acid (21.8 ml, 0.381 mol) were added dropwise to 6-aminocaproic acid (2.5 g, 0.019 mol), and the mixture was refluxed for 30 hrs. The residual acrylonitrile left over from the reaction was removed by evaporating under a reduced pressure, and acetic acid was removed by repeated cycles of adding toluene and evaporating under a reduced pressure. The reaction mixture was diluted with 200 ml of ethyl acetate and washed with water several times. The organic layer thus obtained was dried over Na$_2$SO$_4$, concentrated under reduced pressure, and purified by column chromatography (ethyl acetate:n-hexane=4:1), to obtain the title compound as a sticky brownish syrup (3.5 g).

$^1$H-NMR (CDCl$_3$): δ 1.35-1.49 (m, 4H), 1.65 (t, J=7.5 Hz, 2H), 2.36 (t, J=7.3 Hz, 2H), 2.46-2.84 (m, 6H), 2.86 (t, J=6.7 Hz, 4H), 10.35 (br.s, 1H)

MS (FAB) m/z 238.08 (M$^+$+H)

<2-2> Conversion of Cyano Groups into Amino Groups

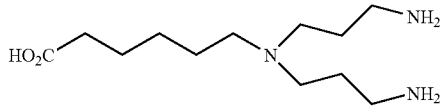

The compound obtained in Preparation Example <2-1> (2.2 g, 1.05 mmol) was dissolved in 45 ml of 95% ethanol, 1 M sodium hydroxide (15 ml) and a Raney Nikel catalyst (4 g) were added thereto, and then, the mixture was allowed to react for 24 hrs under hydrogen atmosphere (50 psi). After the reaction was completed, the mixture was filtered through celite to eliminate the catalyst, and washed with 95% ethanol. The filtrate thus obtained was concentrated under a reduced pressure, to obtain the title compound as a sticky white solid (2.25 g).

$^1$H-NMR (CD$_3$OD): δ 1.31-1.68 (m, 6H), 1.89 (m, 4H), 2.22 (t, J=7.2 Hz, 2H), 2.71-2.76 (m, 6H), 2.98 (t, J=7.5 Hz, 4H)

MS (FAB) m/z 246.15 (M$^+$+H)

<2-3> Protection of Amino Groups with Carbobenzoxy Group (Cbz)

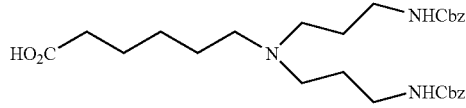

The compound obtained in Preparation Example <2-2> (1.1 g, 6.11 mmol) was dissolved in 45 ml of a 1,4-dioxane: water (2:1) mixture and sodium bicarbonate (2.56 g, 30.57 mmol) was added thereto, followed by slow addition of carbobenzoxychloride (Cbz-Cl)(2.7 ml, 18.34 mmol) to the mixture at 0° C. over 30 min. After stirring at room temperature for 15 hrs, the reaction mixture was concentrated and diluted with 20 ml of water. 10% HCl was added thereto dropwise until the pH of the mixture became 2, and then, extracted with ethyl acetate. The organic layer thus obtained was dried over $Na_2SO_4$, concentrated under a reduced pressure, and purified by column chromatography (dichloromethane:methanol=9:1), to obtain the title compound as a white foamy solid (1.4 g).

$^1$H-NMR (CDCl$_3$): δ 1.33-1.61 (m, 6H), 1.94 (brs, 4H), 2.27 (t, J=6.8 Hz, 2H), 2.93 (br.s, 6H), 3.20-3.22 (m, 4H), 5.01 (s, 4H), 5.65 (br.s, 2H), 7.31 (br.s, 10H)

MS (FAB) m/z 514.21 (M$^+$+H)

Preparation Example 3

Preparation of Aminocaproic Acid Derivative Having Carbobenzoxy Protecting Groups II <3-1> Preparation of N-di-methylacrylated 6-aminocaproic Acid

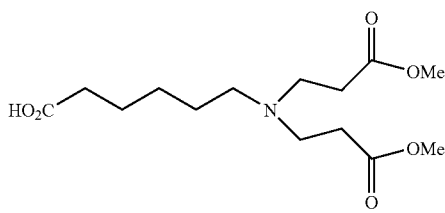

An excess amount of methyl acrylate (77.3 ml, 0.857 mol) and glacial acetic acid (13.1 ml, 0.228 mol) were added dropwise to 6-aminocaproic acid (1.5 g, 0.0114 mol), and the mixture was refluxed for 30 hrs. The remaining methyl acrylate and acetic acid after the reaction were removed by evaporating with added toluene under a reduced pressure. The reaction mixture was diluted with 200 ml of ethyl acetate and washed several times with water. The organic layer thus obtained was dried over $Na_2SO_4$, concentrated under a reduced pressure, and purified by column chromatography (ethyl acetate:n-hexane=4:1), to obtain the tile compound as a viscous brownish syrup (1.85 g).

$^1$H-NMR (CDCl$_3$): δ 1.30-1.62 (m, 6H), 2.30 (t, J=7.4 Hz, 2H), 2.50 (t, J=6.8 Hz, 6H), 2.80-2.86 (m, 4H), 3.66 (s, 6H)

MS (FAB) m/z 304.18 (M$^+$+H)

<3-2> Reaction of Ethylenediamine with the Ester

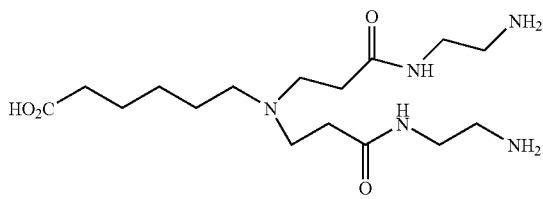

The compound obtained in Preparation Example <3-1> (1.2 g, 3.95 mmol) and ethylenediamine (16 ml, 237.3 mmol) were dissolved in methanol (20 ml) and stirred at room temperature for 72 hrs. The excess amount of ethylenediamine was eliminated by evaporating under a reduced pressure to obtain the title compound as a light brownish syrup (1.4 g).

$^1$H-NMR (CD$_3$OD): δ 1.26-1.64 (m, 6H), 2.16-2.22 (m, 2H), 2.27-2.56 (m, 6H), 2.71-2.88 (m, 8H), 3.29-3.31 (m, 4H)

MS (FAB) m/z 382.19 (M$^+$+Na)

<3-3> Protection of Amino Groups with Carbobenzoxy Group (Cbz)

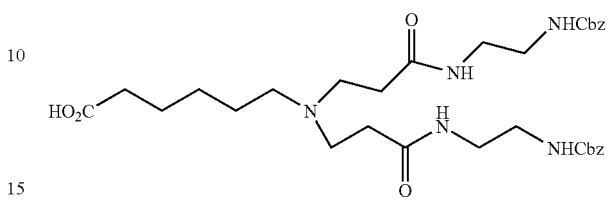

The compound obtained in Preparation Example <3-2> (930 mg, 2.58 mmol) was dissolved in 20 ml of 1,4-dioxane:water mixture (2.5:1), and sodium bicarbonate (1.52 g, 18.11 mmol) was added thereto, followed by slowly adding dropwise 1.4 ml of carbobenzoxychloride (10.34 mmol) to the mixture at 0° C. over a period of 30 min. After stirring at room temperature for 15 hrs, the reaction mixture was concentrated, diluted with 20 ml, of water, and 10% HCl was added dropwise to adjust the pH at ~2, and then, extracted with ethyl acetate. The organic layer thus obtained was dried over $Na_2SO_4$, concentrated under a reduced pressure, and purified by column chromatography (dichloromethane:methanol=9:1), to obtain the title compound as a white solid (1.2 g).

$^1$H-NMR (CD$_3$OD): δ 1.23-1.71 (m, 6H), 2.13 (t, J=6.8 Hz, 2H), 2.30-2.48 (m, 6H), 2.69 (br.s, 4H), 3.21-3.26 (m, 8H), 5.04 (s, 4H), 7.31-7.32 (m, 10H)

MS (FAB) m/z 650.19 (M$^+$+Na)

<3-4> Conversion of Amino Groups into N,N'-di-Boc-guanidine Group

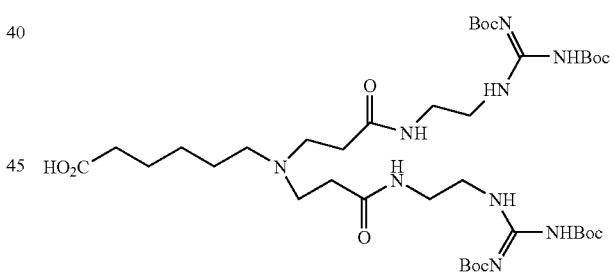

The compound obtained in Preparation Example <3-2> (500 mg, 1.39 mmol) was dissolved in 6 ml of N,N-dimethylformamide, and triethylamine (0.7 ml, 4.86 mmol) and N,N'-di-Boc-N"-triflylguanidine (1.36 g, 3.47 mmol) were added thereto, followed by stirring the mixture at room temperature for 3 days. After the reaction was completed, the reaction mixture was diluted with 100 ml of dichloromethane and successively washed several times with brine and water. The organic layer thus obtained was dried over $Na_2SO_4$, concentrated under a reduced pressure, and purified by column chromatography (dichloromethane:methanol=9:1), to obtain the title compound as a white foamy solid (800 mg).

$^1$H-NMR (CDCl$_3$): δ 1.45-1.66 (m, 42H), 2.41-2.44 (m, 6H), 2.84 (br.s, 4H), 3.40-3.54 (m, 10H), 8.18 (br.s, 2H), 8.64 (br.s, 2H), 11.44 (br.s, 2H)

MS (FAB) m/z 844.33 (M$^+$+H)

Preparation Example 4

Preparation of 2,2,2-trifluoroethyl 3-azidopropionate

<4-1> Preparation of 2,2,2-trifluoroethyl 3-bromopropionate

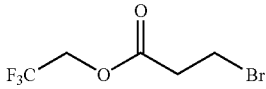

2,2,2-Trifluoroethanol (15 ml, 0.15 mol) and triethylamine (4.5 ml, 32.12 mmol) were added to 30 ml of dichloromethane, and cooled to 0° C. After 10 min, 2.94 ml of 3-bromopropionyl chloride (29.2 mmol) was added dropwise thereto. The mixture was warmed to room temperature and stirred for 5 hrs. After the reaction was terminated by addition of water, the mixture was extracted with ethyl acetate, and the solvent was evaporated under a reduced pressure. The solid impurities were removed by filtration to obtain the title compound as a liquid (3.53 g).

$^1$H-NMR (CDCl$_3$): δ 3.05 (t, J=6.7 Hz, 2H), 3.60 (t, J=6.7 Hz, 2H), 4.54 (q, J=8.4 Hz, 2H)

<4-2> Preparation of 2,2,2-trifluoroethyl 3-azidopropionate

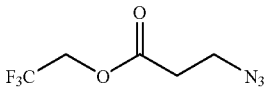

The compound obtained in Preparation Example <4-1> (3.71 g, 15.8 mmol) was dissolved in 15 ml of N,N-dimethylformamide, and sodium azide (2.72 g, 63.2 mmol) and tetrabutylammonium iodide (0.69 g, 3.2 mmol) were added thereto, followed by stirring the mixture for 12 hrs at room temperature. After the reaction was terminated by addition of water thereto, the reaction mixture was washed with brine, and the solvent was evaporated under a reduced pressure. Solid impurities were removed by filtration to obtain the title compound as a yellow liquid (2.76 g).

$^1$H-NMR (CDCl$_3$): δ 2.70 (t, J=6.4 Hz, 2H), 3.63 (t, J=6.4 Hz, 2H), 4.54 (q, J=8.4 Hz, 2H)

MS (FAB) m/z 197.91 (M$^+$+H)

Preparation Example 5

Preparation of Lactose Derivative

<5-1> Preparation of octa-O-benzoyl-α-lactose

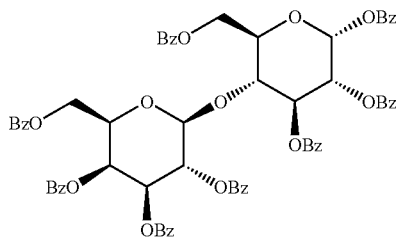

α-Lactose (2.3 g, 6.38 mmol) was dissolved in 30 ml of anhydrous pyridine, benzoyl chloride (8.9 ml, 76.6 mmol) was added thereto at 0° C., and the mixture was stirred for 8 hrs at room temperature. After the reaction was completed, the reaction mixture was extracted with ethyl acetate, and successively washed with 1 N HCl, saturated NaHCO$_3$ and brine. The extract was dried over MgSO$_4$, concentrated under a reduced pressure, and purified by column chromatography (ethyl acetate:n-hexane=1:3), to obtain the title compound as a white solid (7.19 g).

m.p=124~126° C.

[α]$_D$=+113 (c 0.8, chloroform)

$^1$H-NMR (CDCl$_3$): δ 3.73-3.86 (m, 2H, H-4 & H-5'), 3.94 (t, J=6.7 Hz, 1H, H-5), 4.32-4.47 (m, 2H, H-6'), 4.60 (s, 2H, H-6), 4.99 (d, J=7.9 Hz, 1H, H-1'); 5.42 (dd, J=10.3 Hz, 3.3 Hz, 1H, H-3'), 5.66 (dd, J=10.3 Hz, 3.7 Hz, 1H, H-2), 5.78-5.84 (m, 2H, H-2' & H-4'), 6.25 (t, J=9.9 Hz, 1H, H-3), 6.79 (d, J=3.7 Hz, 1H, H-1), 7.20-8.16 (m, 40H, arom)

<5-2> Preparation of 2,3,6,2',3',4',6'-hepta-O-benzoyl lactose

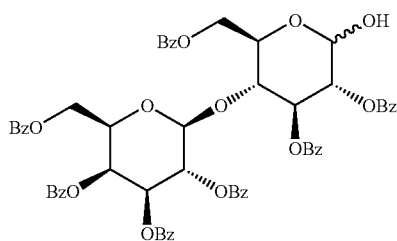

The compound obtained in Preparation Example <5-1> (1 g, 0.85 mmol) was dissolved in 10 ml of a methanol:tetrahydrofuran mixture (3:7), and gaseous ammonia was bubbled thereto at 0° C. for 10 min. The reaction mixture was warmed to room temperature and stirred for 12 hrs. After the reaction was completed, the mixture was concentrated under a reduced pressure, and purified by column chromatography (ethyl acetate:n-hexane=1:1), to obtain the title compound as a white foamy solid (685.8 mg).

$^1$H-NMR (CDCl$_3$): δ 3.73-3.86 (m, 2H, H-4 & H-5'), 4.07-4.11 (m, H-5' & H-5'), 4.23-4.37 (m, H-6'), 4.44-4.56 (m, H-6), 4.90 (d, J=8.0 Hz, H-1'), 4.94 (d, J=7.9 Hz, 1H, H-1'), 5.26 (dd, J=10.2 Hz, 3.5 Hz, H-3' & H-3'), 5.34 (d, J=1.7 Hz, H-1), 5.41 (dd, J=10.3 Hz, 3.1 Hz, H-2 & H-2), 5.64 (d, J=2.5 Hz, 1H, H-1), 5.70-5.76 (m, H-4' and H-2'), 5.81 (t, J=9.0 Hz, H-3), 6.18 (t, J=9.5 Hz, 1H, H-3), 7.16-7.98 (m, 35H, arom)

MS (FAB) m/z 1093.27 (M$^+$+Na)

Preparation Example 6

Preparation of Aminocaproic Acid Having N,N'-di-Boc-guanidine Groups

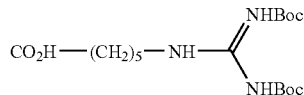

6-Aminocaproic acid (0.53 g, 4.08 mmol) was dissolved in 20 ml of dichloromethane, and triethylamine (1.14 ml, 8.16 mmol) and N,N'-di-Boc-N'''-triflylguanidine (1.23 g, 3.14 mmol) were added thereto, followed by stirring the reaction mixture at room temperature for 24 hrs. After the reaction mixture was successively washed with 2 M NaHSO$_4$ and water, the organic layer was dried over Na$_2$SO$_4$, concentrated under a reduced pressure, and purified by column chromatography to obtain the title compound as a white solid (0.82 g).

$^1$H-NMR (CDCl$_3$): δ 1.48 (s, 24H), 2.35 (t, J=7.4 Hz, 2H), 3.38 (brs, 2H), 8.36 (br.s, 1H, NH), 8.6 10.7 (br.s, 2H, NH, OH)

Example 1

Preparation of Alditol Derivative Having Eight Guanidine Groups I

<1-1> Introduction of Side Chains to Sorbitol by Acylation

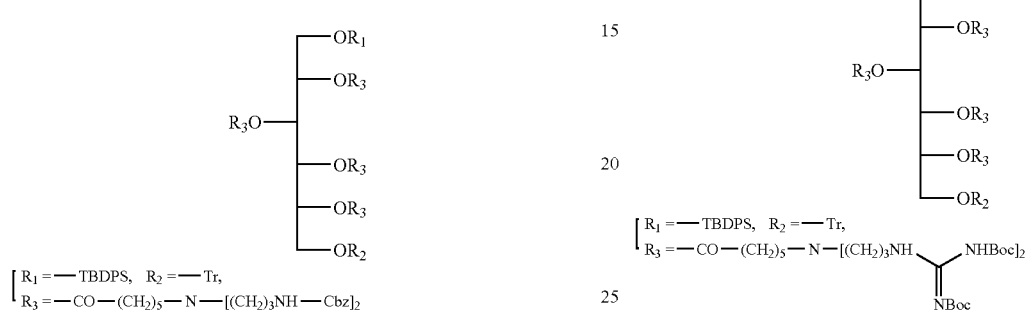

The sorbitol compound with the 1,6-OH groups protected as obtained in Preparation Example 1 (100 mg, 0.15 mmol), the compound obtained in Preparation Example 2 (757.5 mg, 1.2 mmol) and 4-dimethylamino pyridine (27.6 mg, 0.226 mmol) were dissolved in 5 ml of N,N-dimethylformamide, and 1-[3-(dimethylamino)propyl]-ethylcarbodiimide hydrochloride (231.3 mg, 1.2 mmol) was added thereto, followed by stirring the mixture at room temperature for a day. After the reaction was completed, the reaction mixture was extracted with 50 ml, of dichloromethane and the extract was successively washed several times with saturated NaHCO$_3$ solution (30 ml) and water, dried over Na$_2$SO$_4$, concentrated under a reduced pressure, and purified by column chromatography (dichloromethane:methanol=9:1), to obtain the title compound having introduced four side chains at its skeleton as a white foamy solid (263 mg).

$^1$H-NMR (CDCl$_3$): δ 1.01 (s, 9H), 1.17-1.51 (m, 40H), 1.86-2.32 (m, 32H), 3.31 (br.s, 16H), 3.60-3.88 (m, 2H), 3.93-4.12 (m, 2H), 4.79-4.92 (m, 2H), 4.98 (s, 16H), 5.59 (br.s, 8H), 5.61-5.88 (m, 2H), 7.13-7.59 (m, 65H)

MS (MALDI-TOF) m/z 2668.40 (M$^+$+Na)

<1-2> Removal of Carbobenzoxy Groups from Terminal Amino Residues of the Side Chains

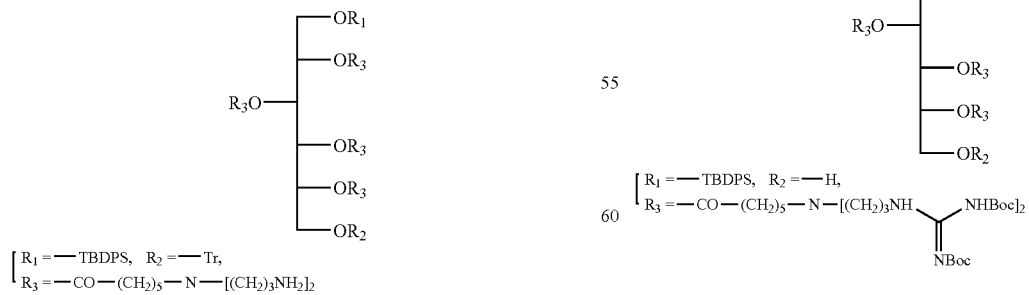

The compound obtained in Example <1-1> (150 mg, 0.056 mmol) was dissolved in 4 ml of methanol and 100 mg of Pd/C was added thereto. The mixture was stirred at room temperature for 15 hrs under H$_2$ atmosphere (50 psi), and filtered through celite to remove the Pd/C catalyst. The filtrate thus obtained was concentrated under a reduced pressure to obtain the title compound as a sticky white solid (87 mg).

$^1$H-NMR (CD$_3$OD): δ 1.02 (s, 9H), 1.16-1.82 (m, 24H), 2.07-2.38 (m, 24H), 3.03-3.28 (m, 40H), 3.56-3.80 (m, 2H), 3.91-4.13 (m, 2H), 4.87-5.13 (m, 2H, merged with CD$_3$OD peak), 5.88 (dd, J=14.2 Hz, 1.9 Hz, 2H), 7.24-7.68 (m, 25H)

<1-3> Conversion of the Amino Groups into N,N'-di-Boc-guanidine Groups

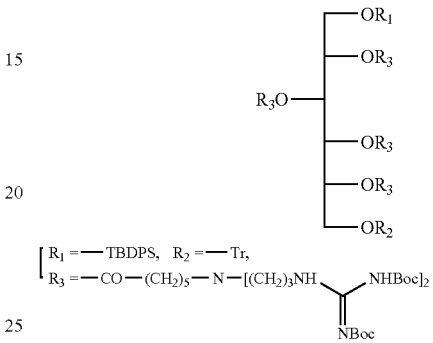

The compound obtained in Example <1-2> (75 mg, 0.0047 mmol) was dissolved in 6 ml of N,N-dimethylformamide, and triethylamine (0.24 ml, 0.166 mmol) and N,N'-di-Boc-N"-triflylguanidine (410 mg, 0.105 mmol) were added thereto, followed by stirring the mixture at room temperature for 2 days. After the reaction was completed, the reaction mixture was diluted with 60 ml of dichloromethane and successively washed with brine and water several times. The organic layer thus obtained was dried over Na$_2$SO$_4$, concentrated under a reduced pressure, and purified by column chromatography (dichloromethane:methanol=10:1), to obtain the title compound having introduced eight guanidine groups as a white foamy solid (104 mg).

$^1$H-NMR (CDCl$_3$): δ 1.03 (s, 9H), 1.18-1.54 (m, 168H), 2.28-2.64 (m, 24H), 2.78-3.28 (m, 24H), 3.59 (br.s, 16H), 3.89-4.21 (m, 4H), 4.82 (br.s, 1H), 5.11 (br.s, 1H), 5.63 (br.s, 1H), 5.89 (br.s, 1H), 7.26-7.67 (m, 25H), 8.39 (br.s, 8H), 11.35 (br.s, 8H)

MS (MALDI-TOF) m/z 3533.34 (M$^+$+Na)

<1-4> Removal of 6-O-trityl Protecting Group

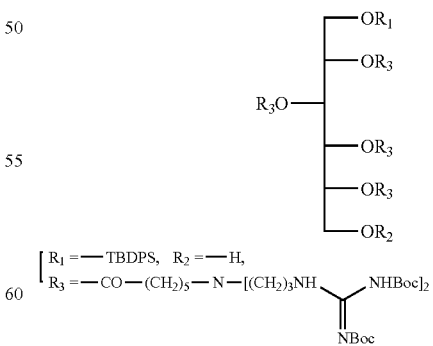

The compound obtained in Example <1-3> (100 mg, 0.0028 mmol) was dissolved in 5 ml, of methanol:dichloromethane mixture (3:1), and a catalytic amount of acetyl chloride was added dropwise thereto, followed by stirring the mixture at room temperature for 4 hrs. After the reaction was completed, 60 mg of NaHCO$_3$ was added to the reaction mixture to neutralize the remaining acid and stirred for 30 min. The reaction mixture was concentrated, diluted with 30 ml of dichloromethane, and washed several times with water. The organic layer was dried over Na$_2$SO$_4$, concentrated under a reduced pressure, and the residue was purified by column chromatography (dichloromethane:methanol=9:1), to obtain the title compound as a sticky white solid (80 mg).

$^1$H-NMR (CDCl$_3$): δ 1.01 (s, 9H), 1.12-1.59 (m, 168H), 2.22-2.60 (m, 24H), 2.77-3.33 (m, 24H), 3.57 (br.s, 16H), 3.88-4.21 (m, 4H), 4.80 (br.s, 1H), 5.13 (br.s, 1H), 5.66 (br.s, 1H), 5.88 (br.s, 1H), 7.25-7.68 (m, 10H), 8.33 (br.s, 8H), 11.42 (br.s, 8H)

MS (MALDI-TOF) m/z 3291.45 (M$^+$+Na)

1-5> Introduction of a Fluorescent Tag

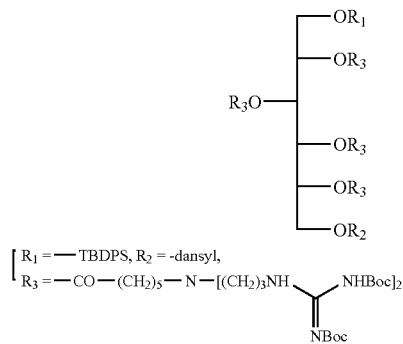

The compound obtained in Example <1-4> (80 mg, 0.024 mmol) and 4-dimethylaminopyridine (7.5 mg, 0.0061 mmol) were dissolved in 3 ml of acetonitrile, and 5-dimethylamino-1-naphthalenesulfonyl chloride (8.5 mg, 0.0032 mmol) was added thereto, followed by stirring the mixture at room temperature for 15 hrs. After the reaction was completed, the reaction mixture was neutralized by adding thereto 10 ml, of saturated NH$_4$Cl solution, extracted with ethyl acetate, and washed with brine and water. The organic layer thus obtained was dried over Na$_2$SO$_4$, concentrated under a reduced pressure, and purified by column chromatography (dichloromethane:methanol=15:1 to 10:1) to obtain the title compound having an introduced fluorescent tag as a sticky yellow solid (80 mg).

$^1$H-NMR (CDCl$_3$): δ 1.02 (s, 9H), 1.13-1.61 (m, 168H), 2.11-2.45 (m, 24H), 2.88 (br.s, 6H), 3.06-3.36 (m, 24H), 3.57 (br.s, 16H), 3.88-4.21 (m, 4H), 4.80 (br.s, 1H), 5.13 (br.s, 1H), 5.66 (br.s, 1H), 5.80 (br.s, 1H), 7.14 (d, J=7.4 Hz, 1H), 7.22-7.78 (m, 27H), 8.16-8.19 (m, 2H), 8.39 (br.s, 8H), 11.45 (b.rs, 8H)

MS (MALDI-TOF) m/z 3523.44 (M$^+$+Na)

<1-6> Removal of N-Boc Protecting Groups from N,N'-di-Boc-guanidine Groups

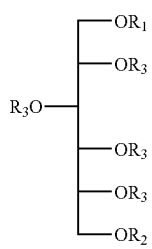

-continued

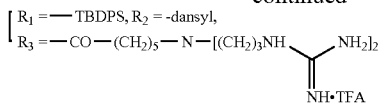

The compound obtained in Example <1-5> (55 mg, 0.0015 mmol) was dissolved in 2 ml of a trifluoroacetic acid:dichloromethane mixture (1:1) and stirred at room temperature for 4 hrs. After the reaction was completed, the mixture was subjected to repeated cycles of adding toluene and evaporating under reduced pressure to completely eliminate trifluoroacetic acid (TFA) therefrom. The reaction mixture was further evaporated under high vacuum for 2 hrs, dissolved in 2 ml of water and freeze-dried, to obtain the title compound having no N-Boc protecting group at the terminal guanidinium groups thereof as a white foamy solid (43 mg)

(Formula 6, R$_3$ = —CO—(CH$_2$)$_n$—N—[(CH$_2$)$_3$NH<sub>\</sub>NH$_2$]$_2$  n = 5).

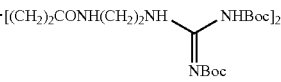

$^1$H-NMR (CD$_3$OD): δ 1.01 (s, 9H), 1.23-1.81 (m, 40H), 1.98 (br.s, 16H), 2.27 (br.s, 8H), 2.81 (s, 6H), 3.19-3.25 (m, 24H), 3.88-4.21 (m, 4H), 4.84 (br.s, 1H), 5.18 (br.s, 1H), 5.60 (b.rs, 1H), 5.81 (br.s, 1H), 7.13-7.78 (m, 13H), 8.16 (br.s, 2H), 8.44 (br.s, 1H)

MS (MALDI-TOF) m/z 1922.52 (M$^+$+Na)

UV λ$_{max}$(H$_2$O, 25° C.) 334 nm

Example 2

Preparation of Alditol Derivative Having Eight Guanidine Groups II

<2-1> Introduction of Side Chains to Sorbitol by Acylation

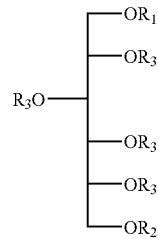

The sorbitol compound with 1,6-OH positions protected as obtained in Preparation Example 1 (75 mg, 0.113 mmol), the compound obtained in Preparation Example 3 (763 mg, 0.905 mmol) and 4-dimethylaminopyridine (20.7 mg, 0.169 mmol) were dissolved in 6 ml of N,N-dimethylformamide, and 1-[3-(dimethylamino)propyl]-ethylcarbodiimide hydrochloride (173.5 mg, 0.905 mmol) was added thereto, followed by stirring the mixture at room temperature for a day. After the reaction was completed, the reaction mixture was extracted with 60 ml of dichloromethane and washed with saturated NaHCO$_3$ and water several times. The organic layer thus obtained was dried over Na$_2$SO$_4$, concentrated under a reduced pressure, and purified by column chromatography (dichloromethane:methanol=9:1), to obtain the title compound having four introduced side chains at its skeleton as a white foamy solid (278 mg).

$^1$H-NMR (CDCl$_3$): δ 1.01 (s, 9H), 1.40-1.53 (m, 168H), 2.19-2.27 (m, 32H), 2.66 (br.s, 16H), 3.31-3.58 (m, 32H), 3.63-3.92 (m, 2H), 4.01 (br.s, 1H), 4.23 (br.s, 1H), 4.88-5.12 (m, 2H), 5.48 (br.s, 1H), 5.73 (br.s, 1H), 7.16-7.58 (m, 25H), 7.94 (br.s, 8H), 8.51 (br.s, 8H), 11.35 (br.s, 8H)

MS (MALDI-TOF) m/z 3989.84 (M$^+$+Na)

<2-2> Removal of 6-O-trityl Protecting Group

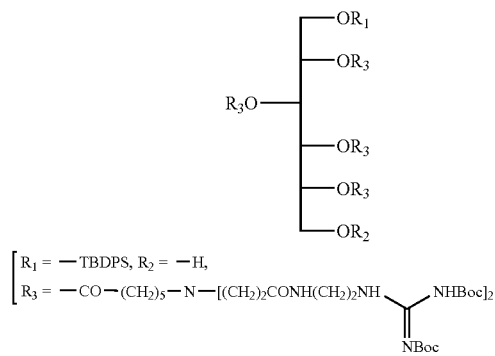

The compound obtained in Example <2-1> (150 mg, 0.0037 mmol) was dissolved in 5 ml of a methanol:dichloromethane mixture (3:1), and a catalytic amount of acetyl chloride was added dropwise thereto, followed by stirring the mixture at room temperature for 4 hrs. NaHCO$_3$ (70 mg) was added to the mixture to neutralize the remaining acid and stirred for 30 min. The reaction mixture was concentrated, diluted with 30 ml, of dichloromethane, and washed with water several times. The organic layer was dried over Na$_2$SO$_4$, concentrated under a reduced pressure, and purified by column chromatography (dichloromethane:methanol=9:1), to obtain the title compound as a sticky white solid (107 mg).

$^1$H-NMR (CDCl$_3$): δ 1.02 (s, 9H), 1.33-1.55 (m, 168H), 2.10-2.23 (m, 32H), 2.68 (br.s, 16H), 3.28-3.55 (m, 32H), 3.60-3.82 (m, 2H), 3.97 (br.s, 1H), 4.20 (br.s, 1H), 4.77-5.09 (m, 2H), 5.33 (br.s, 1H), 5.78 (br.s, 1H), 7.26-7.62 (m, 10H), 7.92 (br.s, 8H), 8.36 (br.s, 8H), 11.45 (br.s, 8H)

<2-3> Introduction of Fluorescent Tag

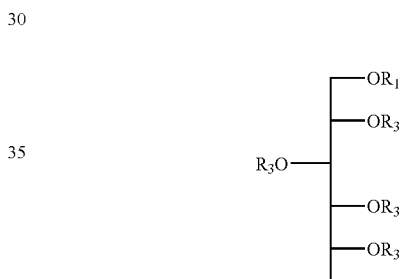

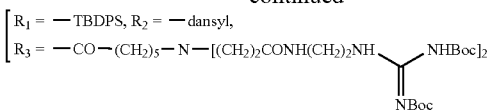

The compound obtained in Example <2-2> (100 mg, 0.0026 mmol) and 4-dimethylamino pyridine (8.2 mg, 0.0067 mmol) were dissolved in 3 ml, of acetonitrile, and 5-dimethylamino-1-naphthalenesulfonyl chloride (9.4 mg, 0.0035 mmol) was added thereto, followed by stirring the mixture at room temperature for 16 hrs. After the reaction was completed, the reaction mixture was neutralized with saturated NH$_4$Cl (10 ml), extracted with ethyl acetate, and washed with brine. The organic layer was dried over Na$_2$SO$_4$, concentrated under a reduced pressure, and purified by column chromatography (dichloromethane:methanol=20:1 to 10:1), to obtain the title compound having an introduced fluorescent tag as a sticky yellow solid (68 mg).

$^1$H-NMR (CDCl$_3$): δ 1.09 (s, 9H), 1.44-1.56 (m, 168H), 2.23 (b.rs, 32H), 2.71 (br.s, 16H), 2.86 (s, 6H), 3.37-3.52 (m, 32H), 3.60-3.84 (m, 2H), 4.01 (br.s, 1H), 4.23 (br.s, 1H), 4.77-5.11 (m, 2H), 5.40 (br.s, 1H), 5.88 (b.s, 1H), 7.15 (d, J=7.5 Hz, 1H), 7.22-7.73 (m, 12H), 7.89-8.14 (m, 10H), 8.36 (br.s, 9H), 11.42 (br.s, 8H)

MS (MALDI-TOF) m/z 1483.99 (M$^+$+Na)

<2-4> Removal of N-Boc Protecting Groups from N,N'-di-Boc-guanidine Groups

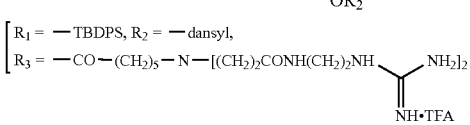

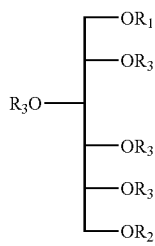

The compound obtained in Example <2-3> (50 mg, 0.0012 mmol) was dissolved in 2 ml of a trifluoroacetic acid:dichloromethane mixture (1:1) and stirred at room temperature for 4 hrs. After the reaction was completed, the reaction mixture was subjected to repeated cycles of adding toluene and evaporating under reduced pressure to completely remove trifluoroacetic acid. After further evaporation under a high vacuum for 2 hrs, the residue was dissolved in 2 ml, of water and subjected to freeze-drying, to obtain the title compound having no N-Boc protecting group at the terminal guanidine groups thereof as a white foamy solid (41 mg)

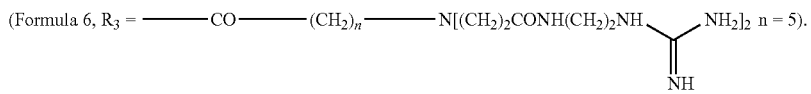

$^1$H-NMR (CD$_3$OD): δ 1.01 (s, 9H), 1.26-1.88 (m, 32H), 2.11-2.32 (m, 16H), 2.72 (br.s, 16H), 2.88 (s, 6H), 3.27 (br.s, 40H), 3.66-3.93 (m, 4H), 4.89-5.11 (m, 2H), 5.56 (br.s, 1H), 5.88 (br.s, 1H), 7.15-7.74 (m, 13H), 8.18 (br.s, 2H), 8.48 (br.s, 1H)

MS (MALDI-TOF) 2145.35 ((M-C$_{12}$H$_{12}$NO$_2$S)$^+$+Na)

UV λ$_{max}$(H$_2$O, 25) 336 nm

Example 3

Preparation of Inositol Derivative Having Eight Guanidine Groups I

After the acetonide protecting group was removed from the myo-inositol intermediate of formula 16, the deprotected intermediate was subjected to acylation, side chains were introduced thereto, and the amino groups at the introduced side chains were converted into guanidine groups according to the same method as described in Examples <1-1> to <1-6>, to obtain the inositol derivative compound having eight guanidine groups (Formula 7).

Example 4

Preparation of Inositol Derivative Having Eight Guanidine Groups II

After the acetonide protecting group was removed from the myo-inositol intermediate of formula 17, the deprotected intermediate was subjected to acylation, side chains were introduced thereto, and the amino groups at the introduced side chains were converted into the guanidine groups according to the same method as described in Examples <1-1> to <1-6>, to obtain the inositol derivative compound having eight guanidine groups (Formula 8).

Example 5

Preparation of Inositol Derivative Having Eight Guanidine Groups III

After the acetonide protecting group was removed from the myo-inositol intermediate of formula 18, the deprotected intermediate was subjected to acylation, side chains were introduced thereto, and the amino groups at the introduced side chains were converted into the guanidine groups according to the same method as described in Examples <1-1> to <1-6>, to obtain the inositol derivative compound having eight guanidine groups (Formula 9).

Example 6

Preparation of Disaccharide Derivative Having Seven Guanidine Groups I

<6-1> Preparation of 1'-O-(3-azidopropionyl)sucrose

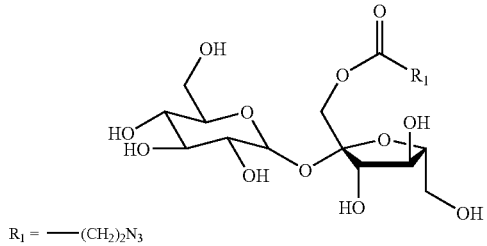

$R_1 = —(CH_2)_2N_3$

Proteinase N (1.00 g, 5.6 U/mg, Fluka) was dissolved in 200 ml, of triply distilled water at a concentration of 5 mg/ml and 0.1 M KOH was added dropwise until pH of the solution became 7.8. The enzyme solution was rapidly cooled with liquid nitrogen and freeze-drying for 48 hrs. sucrose (4.7 g, 3.73 mmol) was dissolved in 11.6 ml of a N,N-dimethylformamide:water mixture (93:7), and the activated proteinase N (691 mg) was added thereto. The compound obtained in Preparation Example 4 (0.90 g, 4.56 mmol) was added to the mixture and stirred at 45° C. for 3 days. After the reaction was completed, the reaction mixture was washed with N,N-dimethylformamide and filtered. The filtrate thus obtained was evaporated under a reduced pressure and purified by column chromatography (dichloromethane:acetone:methanol:water=14:5:5:1), to obtain the title compound as a yellow foamy solid (1.25 g).

$^1$H-NMR (CD$_3$OD): δ 2.65 (t, J=6.3 Hz, 2H, H), 3.30-3.43 (m, 2H, H2, H4), 3.59 (t, J=6.3 Hz, 2H, H), 3.65-3.83 (m, 7H, H5, H6, H6', H'5, H6, H3, H6'), 4.02-4.09 (m, 2H, H3', H4'), 4.21 (d, J=12.0 Hz, 1H, H1'), 4.41 (d, J=12.0 Hz, H1'), 5.40 (d, J=3.8 Hz, 1H, H1)

MS (FAB) m/z 462.09 (M$^+$+Na)

<6-2> Introduction of Side Chains by Acylation

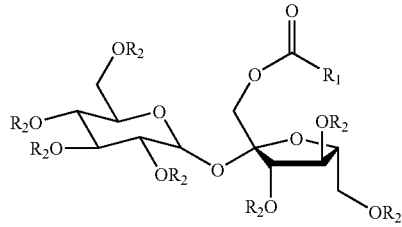

$\begin{bmatrix} R_1 = —(CH_2)_2N_3, \\ R_2 = —CO—(CH_2)_5—NHBoc \end{bmatrix}$

The compound obtained in Example <6-1> (200 mg, 0.46 mmol) and 4-dimethylamino pyridine (84 mg, 0.68 mmol) were dissolved in 5 ml of N,N-dimethylformamide, and 6-Boc-aminocaproic acid (2.05 g, 10.1 mmol) and 1-[3-(dimethylamino)propyl]-ethylcarbodiimide hydrochloride (1.75 g, 9.1 mmol) were added thereto, followed by stirring the mixture at room temperature for 3 days. After the reaction was completed, the reaction mixture was extracted with dichloromethane, and the extract was washed several times with saturated NaHCO$_3$ and water. The organic layer was dried over Na$_2$SO$_4$, concentrated under a reduced pressure, and purified by column chromatography (ethyl acetate:n-hexane=1:1), to obtain the title compound as a colorless foamy solid (459 mg).

$^1$H-NMR (CDCl$_3$): δ 1.43 (s, 63H, 7xt-Bu), 1.72-1.87 (m, 14H), 2.28 2.49 (m, 14H), 2.66 (t, J=6.3 Hz, 2H, H), 3.11-3.15 (m, 14H), 3.62 (t, J=6.3 Hz, 2H, H), 4.16-4.34 (m, 8H), 5.02-5.14 (m, 2H), 5.37-5.46 (m, 3H), 5.65 (brs, 1H)

MS (FAB) m/z 1954.58 (M$^+$+Na)

<6-3> Removal of N-Boc Protecting Groups from Terminal Amino Groups of Side Chains

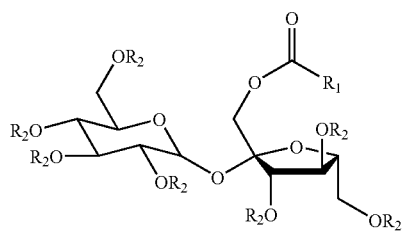

$\begin{bmatrix} R_1 = —(CH_2)_2N_3, \\ R_2 = —CO—(CH_2)_5—NH_2·HCl \end{bmatrix}$ The compound obtained in Example <6-2> (50.6 mg, 28.98 μmol) was dissolved in 1.5 ml, of ethyl acetate saturated with gaseous HCl and stirred at room temperature for 30 min. The mixture was evaporated under a reduced pressure, to obtain the title compound as a white solid (45 mg).

$^1$H-NMR (CD$_3$OD): δ 1.44-1.72 (m, 42H), 2.44 (br.s, 14H), 2.70 (br.s, 2H), 2.96 (br.s, 14H), 3.62 (m, 2H), 4.23-4.33 (m, 9H), 5.12 (br.s, 1H), 5.38 5.61 (m, 3H), 5.72 (s, 1H)

MS (FAB) m/z 1231.94 (M$^+$+H)

<6-4> Conversion of Amino Groups into N,N'-di-Boc-guanidine Groups

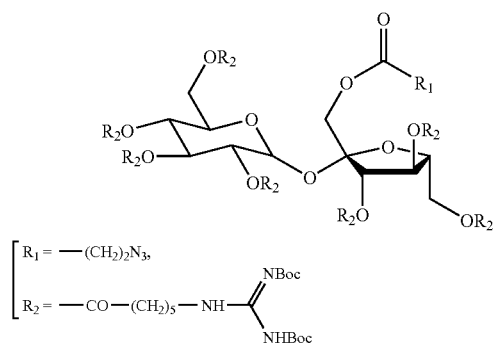

The compound obtained in Example <6-3> (20 mg, 0.013 mmol) was dissolved in 1.5 ml of N,N-dimethylformamide, and triethylamine (0.056 ml, 0.40 mmol) and N,N'-di-Boc-N''-triflylguanidine (0.11 g, 0.28 mmol) were added thereto, followed by stirring the mixture at room temperature for 3 days. After the reaction was completed, the reaction mixture was diluted with ethyl acetate, washed with 2M NaHSO$_4$ and brine, dried over Na$_2$SO$_4$, concentrated under a reduced pressure, and purified by column chromatography (ethyl acetate:n-hexane=1:2), to obtain the title compound as a white foamy solid (24.2 mg).

$^1$H-NMR (CDCl$_3$): δ 1.49 (m, 168H), 2.23-2.42 (m, 14H), 2.63-2.67 (t, J=6.4 Hz, 2H), 3.40-3.41 (m, 14H), 3.59-3.63 (t, J=6.4 Hz, 2H), 4.22-4.33 (m, 6H), 4.91 (m, 1H), 5.08 (m, 1H), 5.33-5.47 (m, 3H), 5.62-5.63 (m, 1H), 8.31 (s, 7H), 11.50 (s, 7H)

MS (FAB) m/z 2948.75 (M$^+$+Na)

<6-5> Introduction of Side Chains Having N,N'-di-Boc-guanidine Groups by Acylation

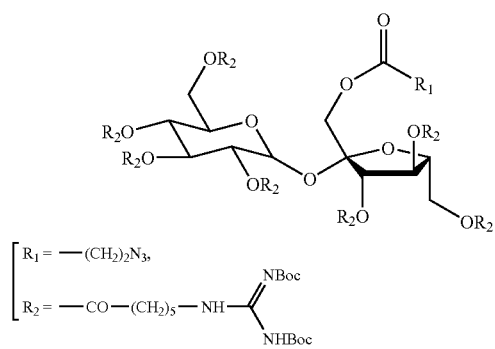

The compound obtained in Example <6-1> (46.9 mg, 0.107 mmol) and 4-dimethylamino pyridine (20 mg, 0.16 mmol) were dissolved in 4 ml of N,N-dimethylformamide, and the compound obtained in Preparation Example 6 (0.74 g, 1.98 mmol) and 1-[3-(dimethylamino)propyl]-ethylcarbodiimide hydrochloride (0.41 g, 2.14 mmol) were added thereto, followed by stirring the mixture at room temperature for 3 days. After the reaction was completed, the reaction mixture was extracted with dichloromethane and the extract was washed with 2 N NaHSO$_4$ and brine, dried over Na$_2$SO$_4$, concentrated under a reduced pressure, and purified by column chromatography (ethyl acetate:n-hexane=1:2), to obtain the title compound as a white foamy solid (229.1 mg), which was identical to that of Example <6-4>.

<6-6> Conversion of Azido Group into Amino Group

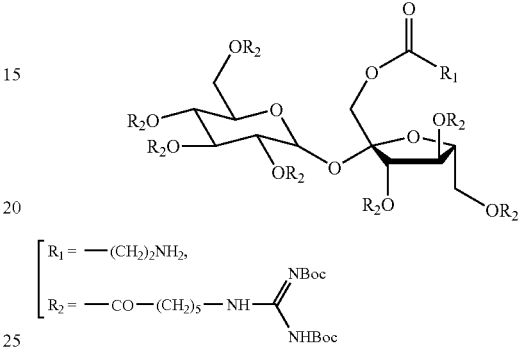

The compound obtained in Example <6-4> or <6-5> (39.1 mg, 0.0134 mmol) was dissolved in ethanol, and 60 mg of a Pd/C catalyst was added thereto, followed by stirring the mixture at room temperature for 2 hrs under hydrogen atmosphere (30 psi). After the reaction was completed, the reaction mixture was filtered through celite to remove the Pd/C catalyst, and concentrated under a reduced pressure, to obtain the title compound as a white solid (36.2 mg).

$^1$H-NMR (CDCl$_3$): δ 1.38-1.70 (m, 168H), 2.23-2.36 (m, 14H), 2.75-2.89 (m, 4H), 3.04 (br.s, 2H), 3.40 (s, 14H), 4.17-4.32 (m, 6H), 4.92 (d, 1H), 5.04-5.11 (t, J=9.6 Hz, 1H), 5.34-5.46 (m, 3H), 5.62 (s, 1H), 8.31 (s, 7H), 11.50 (s, 7H)

<6-7> Introduction of Fluorescent Tag

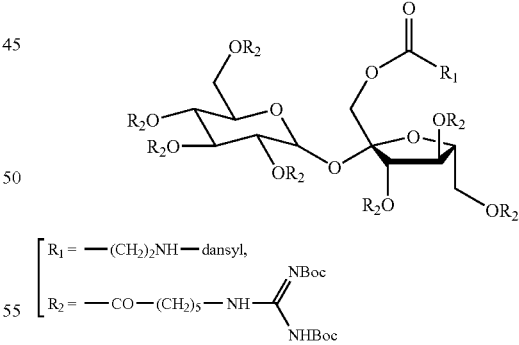

The compound obtained in Example <6-6> (13.5 mg, 0.005 mmol) and triethylamine (1.4 μl, 0.009 mmol) were dissolved in 2 ml of dichloromethane and cooled to 10° C. 5-Dimethylamino-1-naphthalenesulfonyl chloride (1.7 mg, 0.006 mmol) was added to the mixture and stirred at 0° C. for a day. After the reaction was completed, the reaction mixture was subjected to column chromatography (dichloromethane:methanol=150:1), to obtain the title compound as a yellow syrup (12.8 mg).

$^1$H-NMR (CDCl$_3$): δ 1.45-1.59 (m, 168H), 2.29-2.38 (m, 14H), 2.60-2.70 (br.s, 2H), 2.89 (s, 6H), 3.30-3.50 (br.s, 14H), 3.60-3.70 (br.s, 2H), 4.21-4.31 (m, 6H), 5.00-5.15 (br.s, 2H), 5.35-5.48 (m, 4H), 5.64 (s, 1H), 7.18-7.20 (d, J=7.0 Hz, 1H), 7.52-7.55 (m, 2H), 8.22 8.55 (m, 2H), 8.31 (s, 7H), 8.53-8.55 (d, J=8.1 Hz, 1H), 11.50 (s, 7H)

<6-8> Removal of N-Boc Protecting Groups from N,N'-di-Boc-guanidine Groups

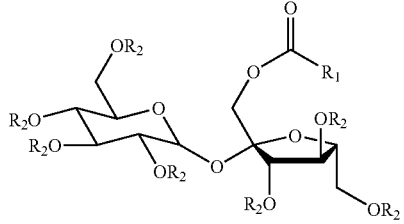

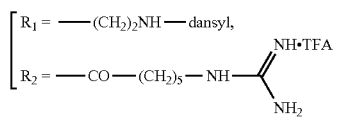

The compound obtained in Example <6-7> (6.5 mg, 0.0021 mmol) was dissolved in 1.3 ml of dichloromethane, and trifluoroacetic acid was added thereto, followed by stirring the mixture at room temperature for 5 hrs. After the reaction was completed, the reaction mixture was subjected to repeated cycles of adding toluene and evaporating under reduced pressure. The product was dissolved in triply distilled water, filtered and freeze-dried, to obtain the title compound as a white foamy solid (4.7 mg) (Formula 10, sucrose skeleton).

$^1$H-NMR (CD$_3$OD): δ 1.27-1.55 (m, 42H), 2.24-2.44 (m, 16H), 2.80 (s, 6H), 3.07 (br.s, 14H), 3.40 (br.s, 1H), 3.55 (br.s, 2H), 4.12-4.24 (m, 6H), 5.31-5.41 (m, 3H), 5.58-5.63 (m, 1H), 7.18-7.20 (d, J=7.6 Hz, 1H), 7.47-7.53 (t, J=8.6 Hz, 2H), 8.10-8.13 (d, J=7.2 Hz, 1H), 8.19-8.22 (d, J=7.2 Hz, 1H), 8.47-8.50 (d, J=8.2 Hz, 1H)

MS (FAB) m/z 1733.07 (M$^+$+H)

UV λ$_{max}$(H$_2$O, 25° C.) 318 nm

Example 7

Preparation of Disaccharide Derivative Having Seven Guanidine Groups II

Amino acid side chains were introduced to the compound obtained in Preparation Example 5 by acylation, and guanidine groups were introduced to the N-terminal of the side chains according to the same method as described in Example 6, to obtain the disaccharide derivative compound having seven guanidine groups (Formula 11, lactose skeleton)

Example 8

Preparation of Alditol Derivative Having Six Guanidine Groups I

<8-1> Introduction of Side Chains to D-sorbitol by Acylation

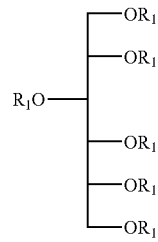

D-Sorbitol (75 mg, 0.411 mmol), 6-(Boc-amino)caproic acid (952 mg, 4.11 mmol), 4-dimethylamino pyridine (110 mg, 0.905 mmol) and 1-[3-(dimethylamino)propyl]-ethylcarbodiimide hydrochloride (789 mg, 4.11 mmol) were dissolved in 2 ml of dichloromethane, and refluxed for 16 hrs. After the reaction was completed, the reaction mixture was diluted with 50 ml of CH$_2$Cl$_2$ and washed several times with saturated NaHCO$_3$ solution and water. The organic layer was dried over Na$_2$SO$_4$, concentrated under a reduced pressure, and purified by column chromatography (ethyl acetate:n-hexane=2:3 to 1:1), to obtain the title compound having introduced six side chains at D-sorbitol as a white solid (547 mg).

$^1$H-NMR (CDCl$_3$): δ 1.28-1.60 (m, 90H), 2.20-2.32 (m, 12H), 3.02 (brs, 12H), 4.04-4.11 (m, 2H), 4.02 (dd, J=14.6 Hz, 2.1 Hz, 1H), 4.34 (dd, J=14.8 Hz, 2.0 Hz, 1H), 4.66 (br.s, 6H), 4.93 (br.s, 1H), 5.16 (br.s, 1H), 5.31-5.42 (m, 2H)

MS (MALDI-TOF) m/z 1483.99 (M$^+$+Na)

<8-2> Removal of N-Boc Protecting Groups from Terminal Amino Groups of Side Chains

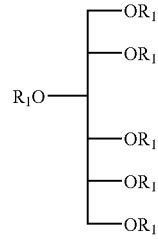

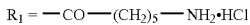

The compound obtained in Example <8-1> (250 mg, 0.171 mmol) was dissolved in 12 ml of ethyl acetate saturated with gaseous HCl, stirred at room temperature for 3 hrs, and the reaction mixture was concentrated under a reduced pressure, to obtain the compound having no N-Boc protecting group at the terminal amino groups at the side chains as a white solid (184 mg).

$^1$H-NMR (CD$_3$OD): δ 1.38-1.40 (m, 12H), 1.59-1.63 (m, 24H), 2.33 (br.s, 12H), 2.86 (br.s, 12H), 4.02-4.14 (m, 2), 4.33-4.48 (m, 2H), 5.11 (br.s, 1H), 5.23 (br.s, 1H), 5.44 (br.s, 2H)

MS (MALDI-TOF) m/z 861.80 (M$^+$+H)

<8-3> Conversion of Amino Groups into N,N'-di-Boc-guanidine Groups

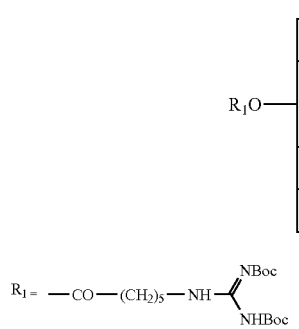

The compound obtained in Example <8-2> (180 mg, 0.166 mmol) was dissolved in 5 ml of a 1,4-dioxane:water mixture (5:1), and triethylamine (0.42 ml, 3.0 mmol) was added thereto, followed by stirring the mixture for 10 min. N,N'-Di-Boc-N''-triflylguanidine (1.17 g, 3.0 mmol) was added to the mixture and stirred at room temperature for 3 days. The reaction mixture was extracted with ethyl acetate, and the extract was washed with water and brine, and dried over $Na_2SO_4$. The extract was concentrated under a reduced pressure and purified by column chromatography (ethyl acetate: n-hexane=2:3 to 1:1), to obtain the title compound having introduced six guanidine groups as a white foamy solid (310 mg).

$^1$H-NMR ($CDCl_3$): δ 1.13-1.55 (m, 90H), 2.23-2.26 (m, 12H), 3.31-3.38 (m, 12H), 4.04-4.06 (m, 2H), 4.24 (dd, J=2.3 Hz, J=14.8 Hz, 2H), 4.95 (brs, 1H), 5.15 (brs, 1H), 5.33-5.35 (m, 2H), 8.26 (brs, 6H), 11.45 (brs, 6H)

MS (MALDI-TOF) m/z 2336.52 ($M^+$+Na)

<8-4> Removal of N-Boc Protecting Groups from N,N'-di-Boc-guanidine Groups

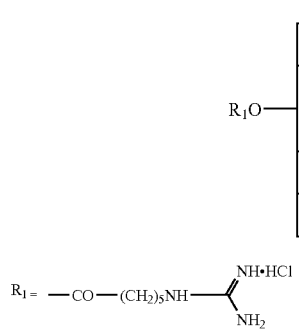

The compound obtained in Example <8-3> (255 mg, 0.110 mmol) was dissolved in 16 ml of ethyl acetate saturated with gaseous HCl and stirred at room temperature for 20 hrs. The reaction mixture was evaporated under a reduced pressure, then dissolved in methanol and evaporated (×3) to obtain the title compound having no N-Boc protecting group at the terminal guanidinium groups thereof as a white foamy solid (146 mg) (Formula 12).

$^1$H-NMR ($CD_3OD$): δ 1.57 (br.s, 36H), 2.26 (br.s, 12H), 3.27 (br.s, 12H), 4.02-4.34 (m, 4H), 5.09-5.33 (m, 4H)

MS (MALDI-TOF) m/z 1113.77 ($M^+$+H)

Example 9

Preparation of Inositol Derivative Having Six Guanidine Groups I

<9-1> Introduction of Side Chains to myo-inositol by Acylation

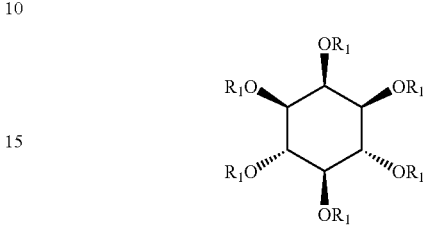

Myo-inositol (33.3 mg, 0.185 mmol), 6-(Boc-amino)caproic acid (362 mg, 1.56 mmol) and 4-dimethylamino pyridine (67.7 mg, 0.554 mmol) were dissolved in 4 ml of $CH_2Cl_2$, and 1-[3-(dimethylamino)propyl]-ethylcarbodiimide hydrochloride (260.8 mg, 1.36 mmol) was added thereto, followed by refluxing for 21 hrs. The reaction mixture was cooled to room temperature, diluted with ethyl acetate, and washed with saturated $NaHCO_3$. The organic layer was separated, dried over $MgSO_4$, concentrated and purified by column chromatography (ethyl acetate:n-hexane=2:3 to 1:1), to obtain the title compound having introduced six side chains to myo-inositol as a colorless oil (206 mg).

$^1$H-NMR ($CDCl_3$): δ 1.1-1.7 (m, 90H), 2.17 (app q, J=6.9 Hz, 10H), 2.42 (t, J=7.2 Hz, 2H), 3.04 (m, 12H), 4.81 (br.s, 6H, 6×NH), 5.08 (dd, J=10.4 Hz, 2.5 Hz, 2H), 5.16 (t, J=9.7 Hz, 1H), 5.44 (t, J=10.1 Hz, 2H), 5.54 (t, J=2.4 Hz, 1H)

MS (MALDI-TOF) m/z 1481.98 ($M^+$+Na)

<9-2> Removal of N-Boc Protecting Groups from Terminal Amino Groups of Side Chains

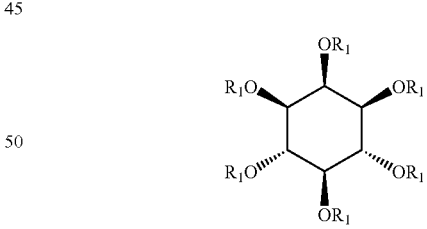

The compound obtained in Example <9-1> (150 mg, 0.103 mmol) was dissolved in 7 ml of ethyl acetate saturated with gaseous HCl and stirred at room temperature for 17 hrs. The reaction mixture was evaporated under a reduced pressure, dissolved in toluene and evaporated (×3) to obtain the title compound having no N-Boc protecting group at the terminal amino groups thereof as a light yellow foamy solid (117 mg).

$^1$H-NMR ($CD_3OD$): δ 1.3-1.9 (m, 36H), 2.21 (br.s, 10H), 2.57 (br.s, 2H), 2.94 (br.s, 12H), 5.3-5.6 (m, 5H), 5.68 (s, 1H)

MS (MALDI-TOF) m/z 881.53 ($M^+$+Na)

<9-3> Conversion of Amino Groups into N,N'-di-Boc-guanidine Groups

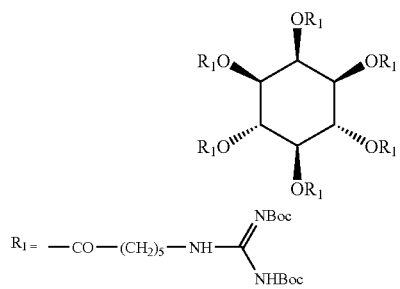

The compound of Example <9-2> (99.2 mg, 0.092 mmol) was dissolved in 6 ml of a 1,4-dioxane:water mixture (5:1), and triethylamine (0.237 ml, 1.7 mmol), and N,N'-di-Boc-N''-triflylguanidine (663 mg, 1.7 mmol) were added thereto, followed by stirring the mixture at room temperature for 3 days. The reaction mixture was concentrated under a reduced pressure, diluted with ethyl acetate, and washed with saturated $NaHCO_3$. The organic layer was, dried over $MgSO_4$, concentrated and purified by column chromatography (ethyl acetate:n-hexane=1:4 to 1:1), to obtain the title compound having introduced six guanidine groups to myo-inositol as a foamy solid (158 mg).

$^1$H-NMR ($CDCl_3$): δ 1.1-1.7 (m, 144H), 2.21 (app.dd, J=11.4, J=6.8 Hz, 10H), 2.48 (t, J=7.4 Hz, 2H), 3.04 (app.q, J=6.2 Hz, 12H), 5.09 (dd, J=10.4, J=2.4 Hz, 2H), 5.18 (t, J=9.7 Hz, 1H), 5.47 (t, J=10.1 Hz, 2H), 5.57 (s, 1H), 8.3 (s, 6H, NH), 11.5 (s, 6H, NHBoc)

MS (MALDI-TOF) m/z 2312.34 ($M^+$+H)

<9-4> Removal of N-Boc Protecting Groups from N,N'-di-Boc-guanidine Groups

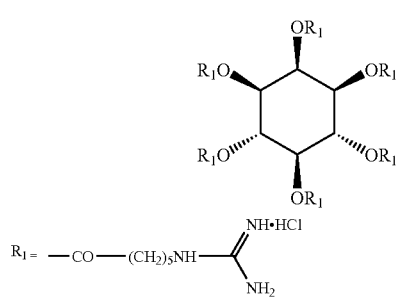

The compound obtained in Example <9-3> (100 mg) was dissolved in 15 ml of ethyl acetate saturated with HCl and stirred at room temperature for 2 days. The reaction mixture was concentrated under a reduced pressure, dissolved in methanol and evaporated (×3), to obtain the title compound having no N-Boc protecting group at the terminal guanidine groups thereof as a white foamy solid (57 mg) (Formula 13).

$^1$H-NMR ($CD_3OD$): δ 1.1-2.8 (m, 48H), 3.0 (m, 12H), 5.23 (m, 6H)

MS (MALDI-TOF) m/z 1111.58 ($M^+$+H)

Example 10

Preparation of Alditol and Inositol Derivatives Having Six Guanidine Groups II

Alditol and inositol derivatives having six guanidine groups (Formulae 12 and 13) identical to those of Examples <8-3> and <9-3> were prepared according to the same method as described in Example <6-5> by using the side chain compound described in the Preparation Example 6, except that D-alditol and myo-inositol isomers were used as the intermediate, respectively.

Example 11

Preparation of Inositol Derivative Having Six Guanidine Groups III

The title compound was prepared as a white solid (45.2 mg) (Formula 14) by employing scyllo-inositol as an intermediate according to the same methods as described in Examples <6-5> and <9-1> to <9-4>.

$^1$H-NMR ($CD_3OD$): δ 1.31-1.56 (m, 36H), 2.34 (s, 12H), 3.15 (s, 12H), 5.62 (s, 6H)

MS (MALDI-TOF) m/z 1111.77 ($M^+$+H)

Test Example 1

Measurement of Membrane Permeability

The permeability through a cell membrane and a nuclear membrane of each of the compounds having dansyl fluorescent tag prepared in the above Examples was measured and compared with that of arginine nonamer (d-$Arg_9$, dansyl-$Arg_9$; Peptron) which is known to efficiently cross biological membranes and also with that of an intermediate having no guanidine group.

A cover glass was placed on a dish plate and mouse macrophage RAW264.7 cells (ATCC T1B-71) were cultured thereon. The cells were stabilized in DMEM (Dulbecco's modified Eagle's medium) supplemented with 10% FBS for 24 hrs, and then cultured in a serum-free medium for 24 hrs to starve the cells. Thereafter, the cells were treated with d-$Arg_9$, the intermediate prepared in Preparation Example <1-2> and any one of the transporter compounds prepared in Examples 1, 2 and 6 at a concentration of 7 μM for 3 min at a constant temperature (23~25° C.). The cells were treated with 100 μg/ml of RNase, and then treated with 2 μg/ml, of propidium iodide at a constant temperature (23~25° C.) for 5 min to dye the nucleus, followed by washing three times with PBS (phosphate buffer solution). The cells were fixed with ethanol for a day, and a section of the collected surface was observed with a confocal microscope equipped with Ar laser (wavelength 458 nm) to detect the fluorescent signal at a magnification of ×400. The results are shown in FIG. 1.

FIG. 1 shows the fluorescent images of RAW264.7 cells treated with d-$Arg_9$ (1); the intermediate prepared in Preparation Example <1-2> having no guanidine group (2); and the compounds of Examples 1 and 6 having 8 and 7 guanidine groups, respectively, in accordance with the present invention (3 and 4). The green color of column A shows the intensity of the fluorescence emitted by the transporter compound inside the cells, the red color of column B shows the dyed nucleus with propidium iodide, and column C shows the merged color between green and red, where the intense yellow color indicates transporter compound present inside the nucleus.

As shown in FIG. 1, the compounds of Examples 1 and 6 display better uptake into the nucleus than d-Arg$_9$, and the intermediate having no guanidine group fails to permeate into the cell.

From these results, it is clear that the compounds showing high membrane permeability in accordance with the present invention can be effectively utilized as molecular transporters for delivering biologically active molecules into cells.

Test Example 2

Measurement of Membrane Permeability of Ionic Complex

The ionic complex (charge-based composition ratio=1:1 to 10:1) of the compound of Example 9 or 10 and fluorescence-tagged cAMP or oligonucleotide were prepared and their permeability through cell membrane were measured according to the same method as described in Test Example 1. The results are observed with a confocal microscope and shown in FIG. 2.

Figure 2:
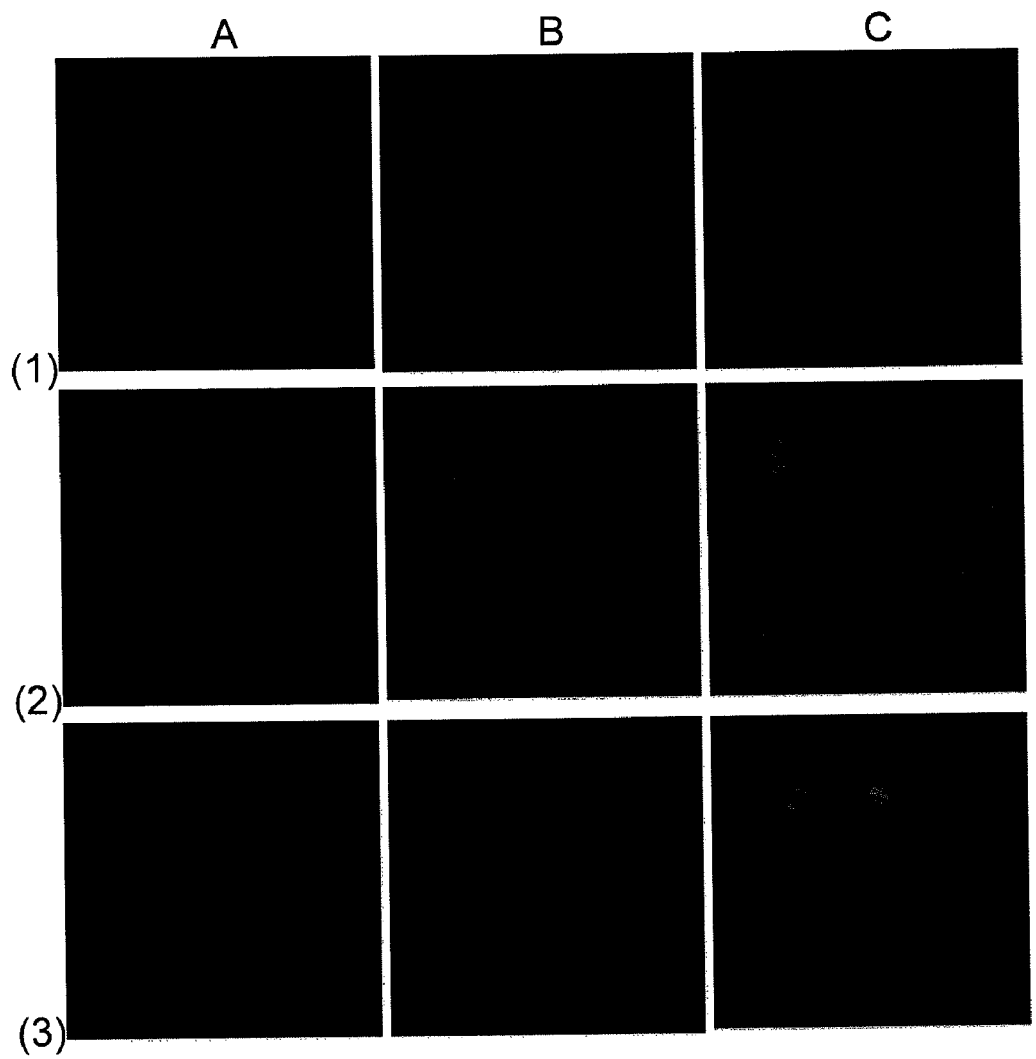
FIG. 2: comparative degrees of cellular and nuclear membrane transmission of various compounds; the fluorescence-tagged anionic cargo substance only (1); the ionic complex of the anionic substance and the transporter compound (charge ration of 1:1, 2); and the ionic complex of the anionic substance and the transporter compound (charge ration of 1:5, 3).

FIG. 2 shows the fluorescence images of RAW264.7 cells treated with the fluorescence-tagged anionic substance only (1); the ionic complex formed from the fluorescence-tagged anionic substance and the molecular transporter at the charge-based composition ratio of 1:1 (2); and the ionic complex formed from the fluorescence-tagged anionic substance and the molecular transporter at the charge-based composition ratio of 1:5 (3). The meanings of columns A, B and C are the same as defined for FIG. 1.

FIG. 2 shows that the ionic complexes having the charge-based composition ratio of 1:5 between an ionic substance and the compound of Example 9 or 10 show good permeability through cell membrane.

These results indicate that the compounds in accordance with the present invention can enhance the permeability through cell membrane in the form of an ionic complex, and accordingly, they can be effectively utilized as molecular transporters for delivering biologically active molecules.

While the invention has been described with respect to the above specific embodiments, it should be recognized that various modifications and changes may be made to the invention by those skilled in the art which also fall within the scope of the invention as defined by the appended claims.

What is claimed is:

1. A disaccharide of formula (3), or a salt thereof:

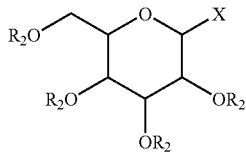
<Formula 3> wherein

X is 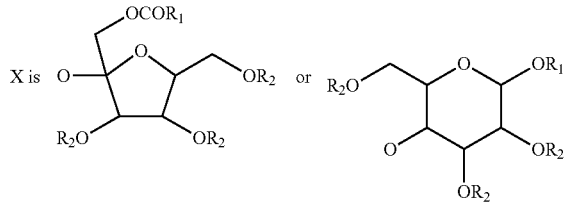

in which $R_1$ is $-(CH_2)_m NHR'$, m is an integer in the range of 2 to 9; R' is selected from the group consisting of H, alkyl, arylalkyl, cycloalkyl, heteroalkyl and a physiologically active molecule;

$R_2$ is 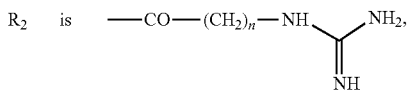

n being an integer in the range of 1 to 12.

2. The disaccharide of claim 1, which is represented by formula (10) or (11), or a salt thereof:

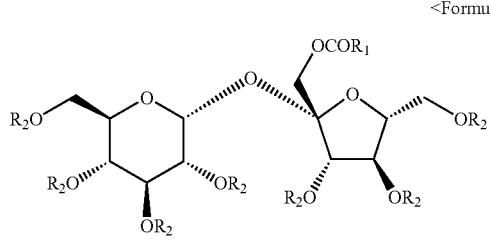
<Formula 10>

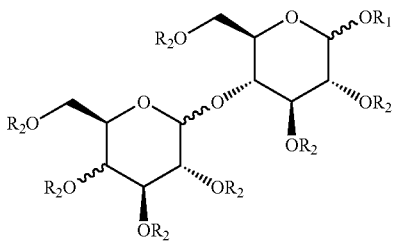
<Formula 11> wherein $R_1$ and $R_2$ are the same as defined in claim 1.

3. The disaccharide of claim 2, wherein the compound of formula (11) has the skeleton of α-lactose, β-lactose or maltose, or a salt thereof.

4. A composition for delivering a biologically active molecule across a biological membrane into a cell, comprising the compound of formula (3) and the biologically active molecule:

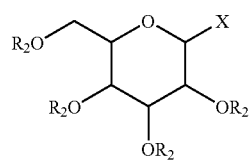
<Formula 3> wherein X and $R_2$ are the same as defined in claim 1, and wherein the biologically active molecule is selected from the group consisting of a peptide, a nucleic acid, a therapeutic molecule, and a diagnostic reagent.

5. The composition of claim 4, wherein the biologically active molecule is an organic compound having a molecular weight ranging from 100 to 1500 g/mol.

6. The composition of claim 4, wherein the biologically active molecule is a peptide or a nucleic acid.

7. The composition of claim 4, wherein the compound of formula (3) forms a conjugate with the biologically active molecule through a covalent bond.

8. The composition of claim 4, wherein the compound of formula (3) forms an ionic complex with the biologically active molecule through ionic bonds.

9. A method for delivering a biologically active molecule across a biological membrane into a cell, wherein the biologically active molecule is one selected from the group consisting of a peptide, a nucleic acid, a therapeutic molecule, and a diagnostic reagent, which comprises the step of employing a compound of formula (3) as a molecular transporter:

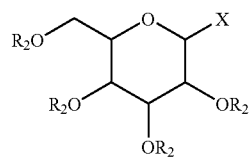
<Formula 3> wherein X and $R_2$ are the same as defined in claim 1, for delivery with the biologically active molecule.

* * * * *

SEQUENCE LISTING

```
<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: amino acid residues 48 to 60 of HIV-1 Tat
      protein

<400> SEQUENCE: 1

Gly Arg Lys Lys Arg Gln Arg Arg Arg Pro Pro Gln Cys
  1               5                  10

<210> SEQ ID NO 2
<211> LENGTH: 16
<212> TYPE: PRT
<213> ORGANISM: Artificial Sequence
<220> FEATURE:
<223> OTHER INFORMATION: amino acid residues 43 to 58 of Antennapedia
      homeodomain

<400> SEQUENCE: 2

Arg Gln Ile Lys Ile Trp Phe Gln Asn Arg Arg Met Lys Trp Lys Lys
  1               5                  10                  15

<210> SEQ ID NO 3
<211> LENGTH: 34
<212> TYPE: PRT
<213> ORGANISM: Artificial Sequence
<220> FEATURE:
<223> OTHER INFORMATION: amino acid residues 267 to 300 of VP 22

<400> SEQUENCE: 3

Asp Ala Ala Thr Ala Thr Arg Gly Arg Ser Ala Ala Ser Arg Pro Thr
  1               5                  10                  15

Glu Arg Asp Arg Ala Pro Ala Arg Ser Ala Ser Arg Pro Arg Arg Pro
             20                  25                  30

Val Glu
```

```
<210> SEQ ID NO 4
<211> LENGTH: 8
<212> TYPE: PRT
<213> ORGANISM: Artificial Sequence
<220> FEATURE:
<223> OTHER INFORMATION: SV40 nuclear localization signal

<400> SEQUENCE: 4

Pro Lys Lys Lys Arg Lys Val Cys
 1               5

<210> SEQ ID NO 5
<211> LENGTH: 17
<212> TYPE: PRT
<213> ORGANISM: Artificial Sequence
<220> FEATURE:
<223> OTHER INFORMATION: Nucleoplasmin nuclear localization signal

<400> SEQUENCE: 5

Lys Arg Pro Ala Ala Ile Lys Lys Ala Gly Gln Ala Lys Lys Lys Lys
 1               5                  10                  15

Cys

<210> SEQ ID NO 6
<211> LENGTH: 10
<212> TYPE: PRT
<213> ORGANISM: Artificial Sequence
<220> FEATURE:
<223> OTHER INFORMATION: NF-kB

<400> SEQUENCE: 6

Pro Met Leu Lys Gln Arg Lys Arg Gln Ala
 1               5                  10

<210> SEQ ID NO 7
<211> LENGTH: 17
<212> TYPE: PRT
<213> ORGANISM: Artificial Sequence
<220> FEATURE:
<223> OTHER INFORMATION: amino acid residues 34 to 50 of HIV-1 Rev

<400> SEQUENCE: 7

Arg Gln Ala Arg Arg Asn Arg Arg Arg Trp Arg Glu Arg Gln Arg
 1               5                  10                  15

Gly

<210> SEQ ID NO 8
<211> LENGTH: 17
<212> TYPE: PRT
<213> ORGANISM: Artificial Sequence
<220> FEATURE:
<223> OTHER INFORMATION: amino acid residues 35 to 49 of FHV Coat

<400> SEQUENCE: 8

Arg Arg Arg Asn Arg Thr Arg Arg Asn Arg Arg Arg Val Arg Arg Gly
 1               5                  10                  15

Cys
```